United States Patent
Ishii et al.

(10) Patent No.: US 10,039,452 B2
(45) Date of Patent: Aug. 7, 2018

(54) OPTICAL SENSOR, OPTICAL TESTING DEVICE, AND OPTICAL CHARACTERISTIC DETECTION METHOD

(71) Applicants: Toshihiro Ishii, Miyagi (JP); Yoichiro Takahashi, Miyagi (JP); Satoru Sugawara, Miyagi (JP); Takeaki Shimokawa, Kyoto (JP); Okito Yamashita, Kyoto (JP); Masaaki Sato, Kyoto (JP)

(72) Inventors: Toshihiro Ishii, Miyagi (JP); Yoichiro Takahashi, Miyagi (JP); Satoru Sugawara, Miyagi (JP); Takeaki Shimokawa, Kyoto (JP); Okito Yamashita, Kyoto (JP); Masaaki Sato, Kyoto (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/913,754

(22) PCT Filed: Sep. 26, 2014

(86) PCT No.: PCT/JP2014/076479
§ 371 (c)(1),
(2) Date: Feb. 23, 2016

(87) PCT Pub. No.: WO2015/046624
PCT Pub. Date: Apr. 2, 2015

(65) Prior Publication Data
US 2016/0242647 A1    Aug. 25, 2016

(30) Foreign Application Priority Data

Sep. 30, 2013 (JP) .................................. 2013-203155
Aug. 11, 2014 (JP) .................................. 2014-163363

(51) Int. Cl.
*A61B 5/00* (2006.01)
*A61B 5/1455* (2006.01)
(Continued)

(52) U.S. Cl.
CPC .......... *A61B 5/0042* (2013.01); *A61B 5/0033* (2013.01); *A61B 5/0073* (2013.01);
(Continued)

(58) Field of Classification Search
CPC .......... G21K 1/08; A61B 6/08; A61B 6/4078; A61B 5/1455; A61B 2018/208
See application file for complete search history.

(56) References Cited

U.S. PATENT DOCUMENTS 5,009,318 A    4/1991  Lepinoy
5,095,386 A *  3/1992  Scheibengraber ....... A61B 6/08
                                              359/668
(Continued)

FOREIGN PATENT DOCUMENTS

CN    101151513 A    3/2008
CN    102287665 A    12/2011
(Continued)

OTHER PUBLICATIONS

European search report dated Jul. 20, 2016 in corresponding European Patent Application No. 14846798.8.
(Continued)

*Primary Examiner* — Catherine Voorhees
*Assistant Examiner* — Natasha Patel
(74) *Attorney, Agent, or Firm* — Cooper & Dunham LLP

(57) ABSTRACT

An optical sensor includes an irradiation system including at least one light irradiator to irradiate light onto an object under test; and a detection system detecting the light that is irradiated from the irradiation system and is propagated in the object under test. Further, the light irradiator irradiates
(Continued)

non-parallel plural light beams on a same position of the object under test.

18 Claims, 28 Drawing Sheets

(51) Int. Cl.
*A61B 5/026* (2006.01)
*A61B 5/16* (2006.01)
*G01N 21/01* (2006.01)

(52) U.S. Cl.
CPC .......... *A61B 5/0261* (2013.01); *A61B 5/1455* (2013.01); *A61B 5/165* (2013.01); *G01N 21/01* (2013.01); *A61B 2562/0238* (2013.01); *A61B 2562/146* (2013.01); *A61B 2562/16* (2013.01)

(56) References Cited

U.S. PATENT DOCUMENTS

| | | | |
|---|---|---|---|
| 6,016,227 A * | 1/2000 | Hopkins | B23K 26/06 219/121.6 |
| 6,466,806 B1 * | 10/2002 | Geva | A61B 5/0095 600/310 |
| 2002/0146873 A1 * | 10/2002 | Tanaka | G02B 27/0905 438/166 |
| 2003/0063783 A1 * | 4/2003 | Higuchi | G06K 9/00046 382/125 |
| 2004/0012788 A1 | 1/2004 | Nakajima et al. | |
| 2004/0081621 A1 | 4/2004 | Arndt et al. | |
| 2005/0277186 A1 * | 12/2005 | Fein | G02B 21/365 435/288.7 |
| 2009/0147373 A1 * | 6/2009 | Rolland | A61B 5/0066 359/665 |
| 2010/0030041 A1 * | 2/2010 | Bruinsma | A61B 5/14532 600/322 |
| 2011/0210270 A1 | 9/2011 | Tajo | |
| 2012/0130215 A1 | 5/2012 | Fine et al. | |
| 2012/0257191 A1 | 10/2012 | Deckenbach et al. | |
| 2013/0194573 A1 | 8/2013 | Ohba et al. | |
| 2014/0126324 A1 * | 5/2014 | Sangawa | G01N 21/4788 367/7 |

FOREIGN PATENT DOCUMENTS

| | | |
|---|---|---|
| JP | H10-086973 | 4/1998 |
| JP | 3779134 | 5/2006 |
| JP | 2008-200226 | 9/2008 |
| JP | 2011-114228 | 6/2011 |
| JP | 2011-179903 | 9/2011 |
| JP | 2012-080975 | 4/2012 |
| JP | 2012-127937 | 7/2012 |
| JP | 2012-132740 | 7/2012 |
| JP | 2012-187358 | 10/2012 |
| JP | 2013-017723 | 1/2013 |
| WO | 2010/150751 A1 | 12/2010 |
| WO | 2012/064326 A1 | 5/2012 |

OTHER PUBLICATIONS

T.Shimokawa, T.Kosaka, O.Yamashita, N.Hiroe, T.Amita, Y.Inoue, and M.Sato, "Hierarchical Bayesian estimation improves depth accuracy and spatial resolution of diffuse optical tomography," Optics Express, vol. 20, No. 18, pp. 20427-20446 (2012).
International Search Report dated Jan. 6, 2015 in PCT/JP2014/076479 filed on Sep. 26, 2014.
Chinese official action (and English translation thereof) dated Jan. 19, 2018 in connection with corresponding Chinese patent application No. 201480052569.0.
Communication pursuant to Article 94(3) EPC dated May 28, 2018 in connection with Europe patent application No. 14846798.8.
Eiji Okada and David T. Delpy: "Near-infrared light propagation in an adult head model. I. Modeling of low-level scattering in the cerebrospinal fluid layer", Applied Optics, vol. 42, No. 16, Jun. 1, 2003 (Jun. 1, 2003), pp. 2906-2914.

* cited by examiner

WATER TANK FOR PHANTOM

LAYOUT OF TRANSPARENT WINDOWS

IN-BODY PROPAGATION ANGLE

SENSITIVITY DISTRIBUTION 2

IN-BODY PROPAGATION ANGLE

ACTUAL POSITION OF LIGHT ABSORPTION BODY

ESTIMATION RESULT

COMPARATIVE EXAMPLE

ACTUAL POSITION OF LIGHT ABSORPTION BODY

ESTIMATION RESULT

COMPARATIVE EXAMPLE

OPTICAL SIMULATION RESULT

COMPARATIVE EXAMPLE

THIS EMBODIMENT

LIGHT PROPAGATION FROM AIR
(REFRACTIVE INDEX: 1) TO LIVING BODY (1.37)

LIGHT PROPAGATION FROM RESIN
(REFRACTIVE INDEX: 1.5) TO LIVING BODY (1.37)

FIG.31
ESTIMATION RESULT
| DEPTH (mm) | COMPARATIVE EXAMPLE | EXAMPLE 2 |
|---|---|---|
| 2 | × | ○ |
| 4 | × | ○ |
| 6 | × | ○ |
| 8 | × | ○ |
| 10 | × | ○ |
| 12 | × | ○ |
| 14 | × | ○ |
| 16 | × | ○ |
| 17 | × | × |
FIG.32
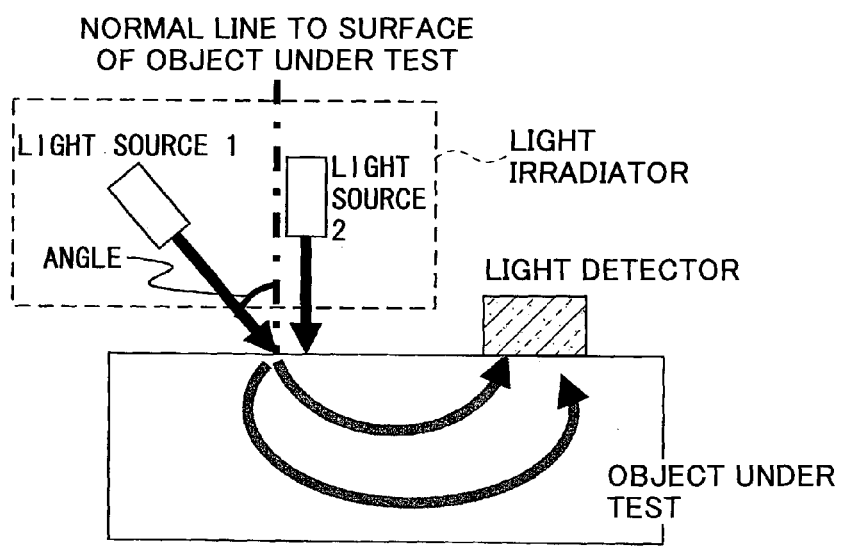
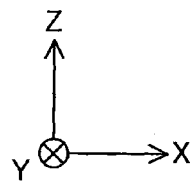

LAYOUT OF FOUR DIVIDED PD ARRAY CHIP

LAYOUT OF SURFACE EMITTING LASER ARRAY CHIP

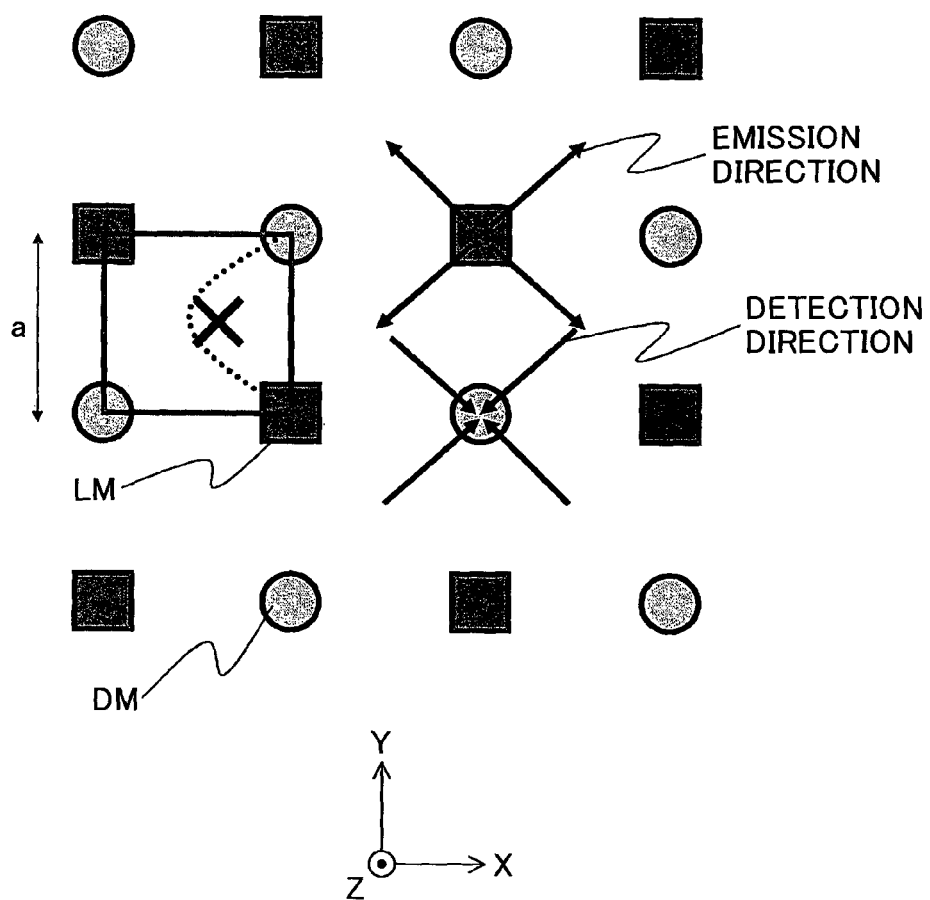

OPTICAL SENSOR, OPTICAL TESTING DEVICE, AND OPTICAL CHARACTERISTIC DETECTION METHOD

TECHNICAL FIELD

The present invention relates onto an Optical sensor, an optical testing device, and an optical characteristic detection method, and more particularly to an optical sensor including an irradiation system to irradiate light to an object under test and a detection system to detect the light irradiated from the irradiation system and propagated through the object under test, an optical testing device including the optical sensor, and an optical characteristic detection method using the optical testing device.

BACKGROUND ART

There has been known a living body optical measurement device that irradiates light onto an object under test (living body) and detects the light propagated through the object under test (see, for example, Patent Document 1).

In the living body optical measurement device, in order to achieve higher resolution, the pitches between plural probes that are attached to the object under test are made narrow.

SUMMARY OF THE INVENTION

Problems to be Solved by the Invention

However, in the living body optical measurement device disclosed in Patent Document 1, the density of the plural probes (the number of the probes per unit area) is increased, so that the attachment performance of the probes to the object under test is remarkably impaired.

Means for Solving the Problems

According to an aspect of the present invention, an optical sensor includes an irradiation system including at least one light irradiator to irradiate light onto an object under test; and a detection system detecting the light that is irradiated from the irradiation system and is propagated in the object under test. Further, the light irradiator irradiates non-parallel plural light beams on a same position of the object under test.

Effects of the Present Invention

According to an aspect of the present invention, it may become possible to obtain higher resolution without degrading the attachment performance to the object under test.

BRIEF DESCRIPTION OF THE DRAWINGS

FIG. 31 is a drawing illustrating an estimation result of inverse problem estimation according to the example 2;

FIG. 32 is a drawing illustrating an operation of the optical sensor according to the first embodiment;

FIG. 37 is a drawing illustrating irradiation directions of the light source modules and detecting directions of the detection sensors in an optical sensor according to the fourth embodiment;

BEST MODE FOR CARRYING OUT THE INVENTION

First Embodiment

Figure 1:
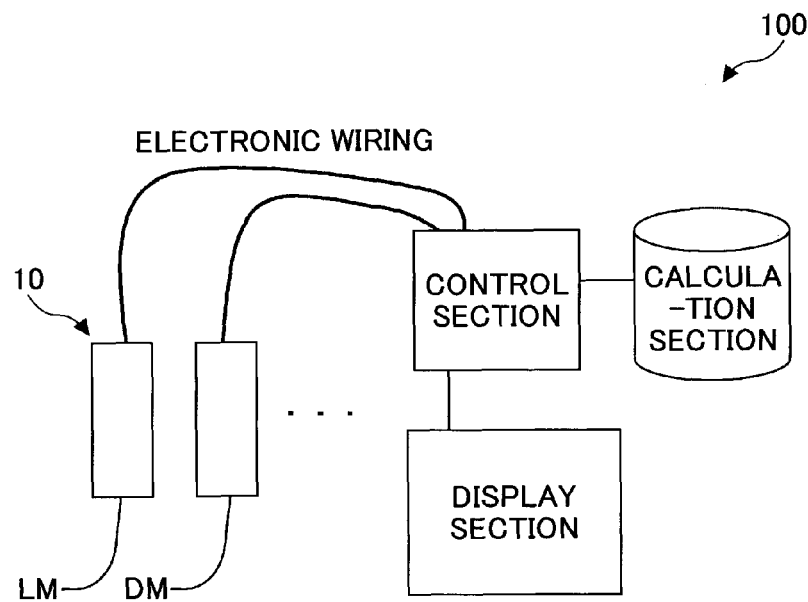
FIG. 1 is a drawing illustrating a schematic configuration of an optical testing device according to a first embodiment of the present invention.

In the following, a first embodiment of the present invention is described with reference to FIGS. 1 through 32. FIG. 1 illustrates a schematic configuration of an optical testing device 100 according to the first embodiment.

As an example, the optical testing device 100 is used in Diffuse Optical Tomography (DOT). The DOT refers to a technique in which light is irradiated onto an object under test (scattering body) such as, for example, a living body and the light propagated in the object under test is detected, so that an optical characteristic in the object under test is estimated. Especially, it is expected to be used to assist in differential diagnosis of depression and as an auxiliary component by detecting blood flow in a brain. In the DOT, when the resolution is improved, it becomes possible to recognize brain functions in more detail. Due to this reason, many research institutions have been actively conducting research for the improvement of the resolution.

Figure 38:
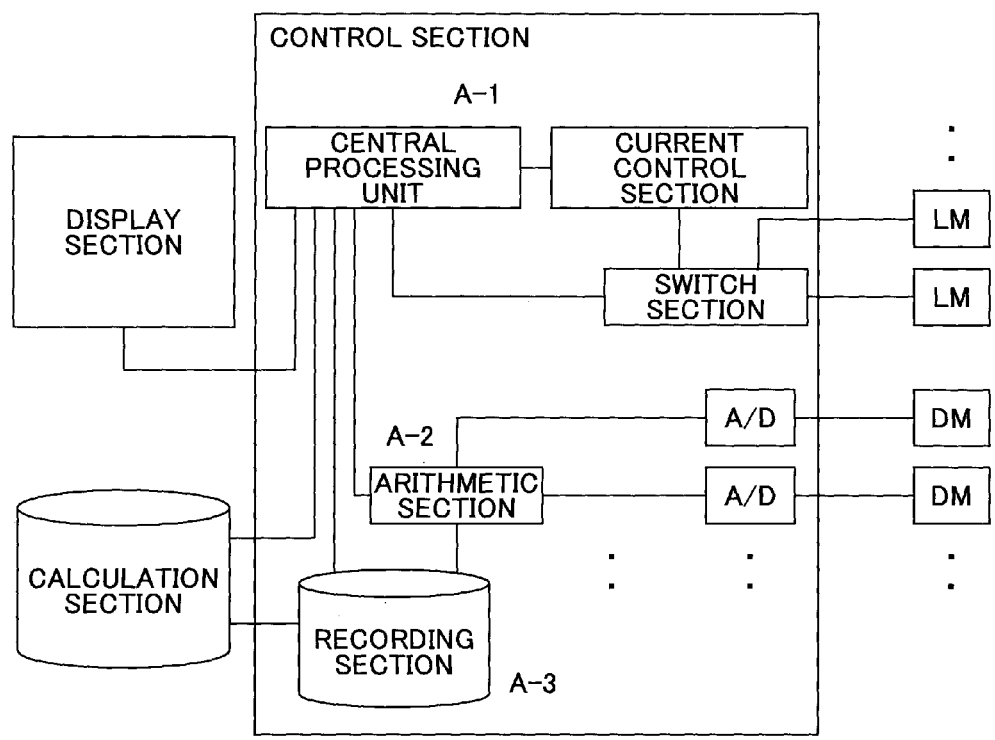
FIG. 38 is a block diagram illustrating a configuration of a control section.

As illustrated in FIG. 1, the optical testing device 100 includes an optical sensor 10, a control section, a display section, a calculation section, etc. The optical sensor 10 includes a light source module LM, which has plural light emitting sections, and a detection module DM. The control section has a configuration as illustrated in FIG. 38. In the control section, a switch section is controlled based on the information from a Central Processing Unit (A-1), so that the LM to be irradiated is selected. In this case, current to be supplied to the light source module LM via the switch section is controlled to be set to a desired value by a current control section. A detection result (data) in the detection module DM is A/D converted, so that calculations such as an averaging process are performed by an arithmetic section (A-2). The arithmetic results are sequentially recorded in a recording section (A-3).

In the description, a term "probe" may be used when the light source module LM and the detection module DM are not distinguished from each other. Further, in the description, terms "pseudo living body", "living body", and "object under test" are used when appropriate. However, note that the "pseudo living body", and the "living body" are examples of the "object under test".

The optical sensor 10 can be generally used as a sensor to detect a light absorption body in an object under test. However, the object under test having the highest utility value is a living body. However, it is not always easy to detect a position of blood flow (light absorption body) in a living body by using an optical sensor, so that, when a living body is an object under test, it is difficult to ensure the effect (detection accuracy) by the optical sensor 10.

In this regard, according to this embodiment, a pseudo living body which is a cloudy liquid contained in a water tank (hereinafter may also be referred to as a "phantom") is employed as an object under test for which it is easy to ensure the detection accuracy.

In the following, an example 1 in this embodiment is described.

Example 1

In example 1, a method is employed in which light beams from light emitting sections are deflected by a prism, so that the incident angles of the light beams differ from each other.

Figure 2:
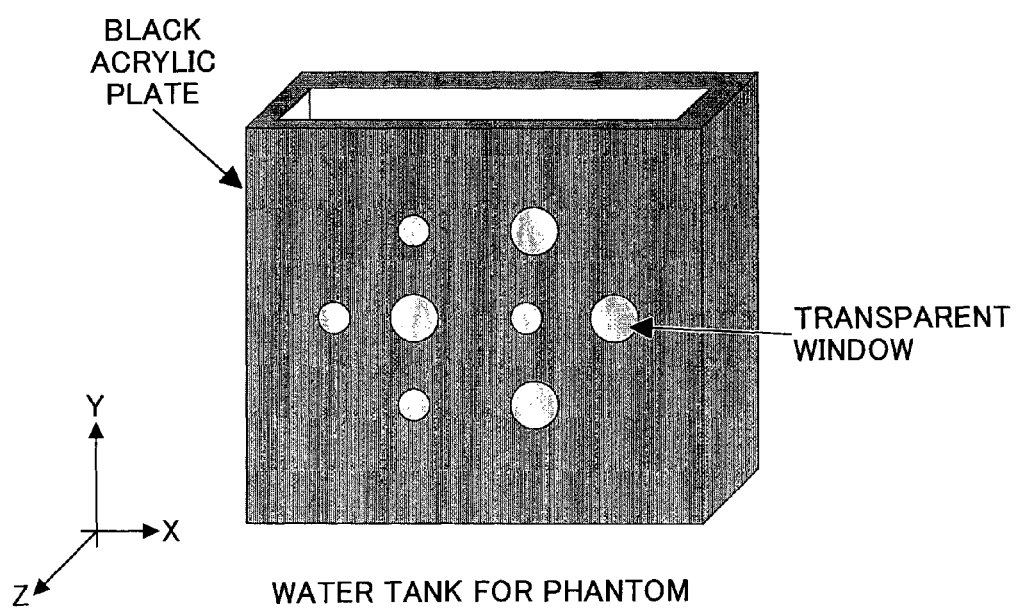
FIG. 2 is a drawing illustrating a water tank for a phantom.

Here, as illustrated in FIG. 2, transparent windows made of transparent acrylic plates are provided on one side surface (the wall in +Z direction) of a water tank including walls made of black acrylic plates. The inside of the water tank is filled with an Intralipid water solution (diluted Intralipid 10% concentration with water). Namely, the pseudo living body used in the example 1 is the Intralipid water solution.

Black ink is dropped in the Intralipid water solution that has filled in the water tank so that the black ink is approximately 20 ppm so as to obtain an absorption coefficient and a scattering coefficient which are substantially the same as those of a living body. Then, a light absorption body having black color which simulates blood flow is dipped into the white Intralipid water solution. Here, it is assumed that the light absorption body is a black spherical object having a diameter of approximately 5 mm such as black polyacetal. In order to control the position of the spherical object, the spherical object is fixed to a thin metal bar having a diameter of 1 mm connected to an automatic stage. The positions of the probes on the transparent windows are accurately determined, so that the probes are attached to the transparent windows.

Here, the volume (size) of the water tank is 140 mm×140 mm×60 mm. The thickness of the black acrylic plates is 4 mm. The eight transparent windows consist of two type of circular transparent windows A and B having different sizes from each other. Both the transparent windows A and the transparent windows B are four in number. The diameter of the transparent window A is 9 mm, and the diameter of the transparent window B is 12 mm. Both the transparent window A and the transparent window B are 1.5 mm thick.

Figure 3:
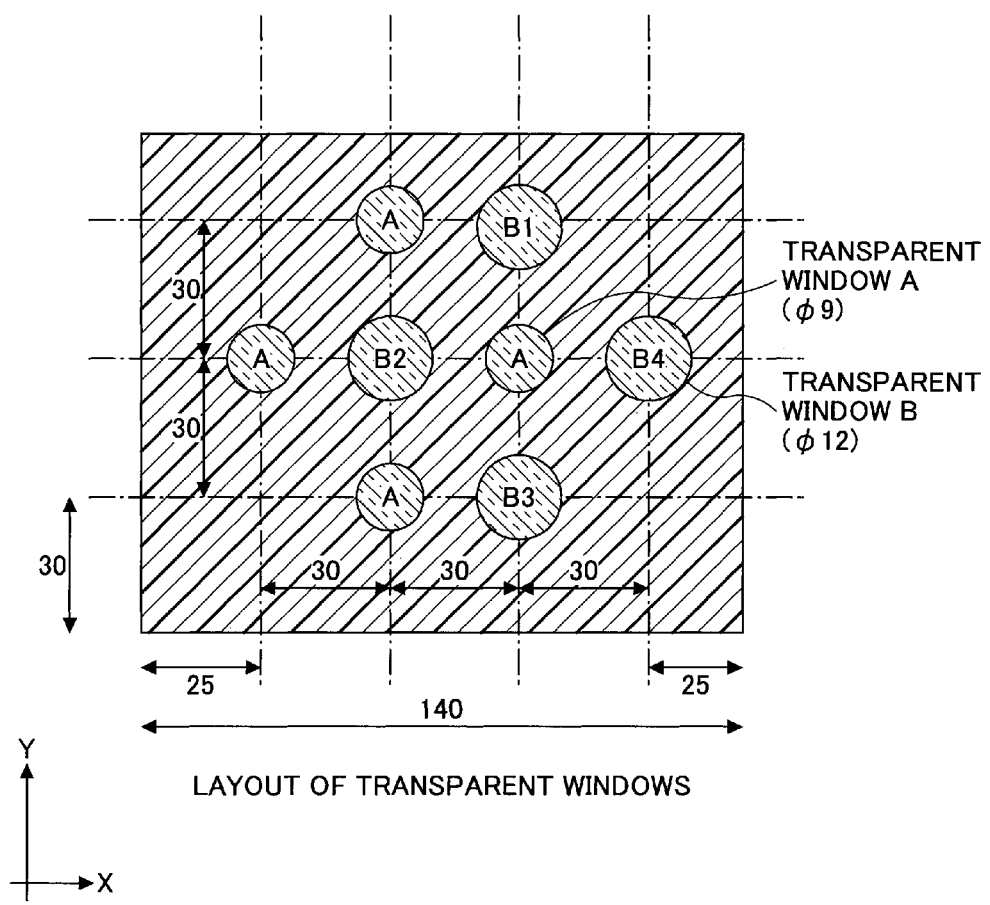
FIG. 3 is a drawing illustrating layout of transparent windows.

FIG. 3 illustrates a layout of the eight transparent windows. Those eight windows are arrange in a lattice manner so that the transparent windows A and B are arranged next to each other at the same distances in Y axis and Y axis directions. Here, the transparent windows A are equipped with the respective detection modules DM and the transparent windows B (B1 through B4) are equipped with the respective light source modules LM. The distance between the centers of the adjacent transparent windows is 30 mm.

Figure 4:
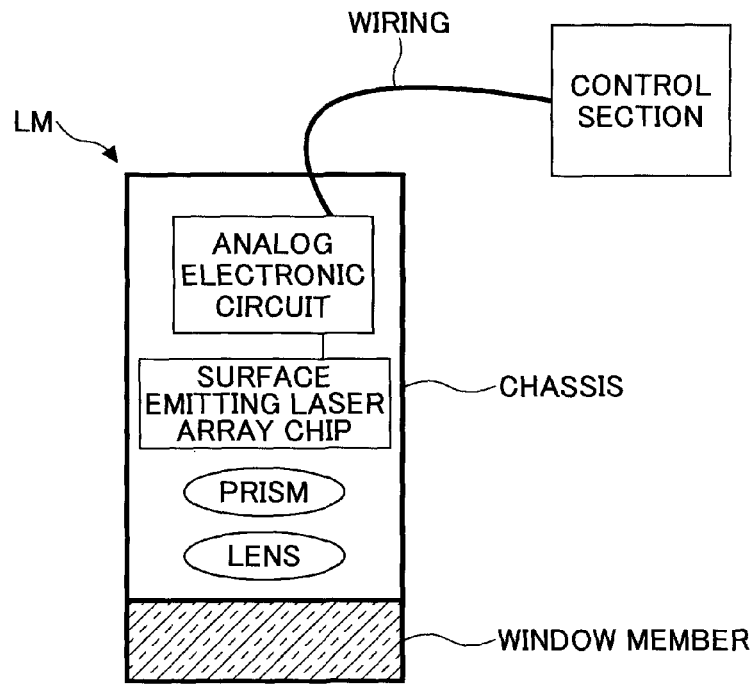
FIG. 4 is a first drawing illustrating a schematic configuration of a light source module according to an example 1.

As illustrated in FIG. 4, the light source module LM includes a lens, a prism, a ceramic package (not shown) in which a surface emitting laser array chip is mounted, a flexible printed circuit board (not shown) in which the ceramic package and an analog electronic circuit are mounted, wirings and connector sections (not shown) connected to the flexible printed circuit board, a chassis containing those elements, a window member made of a transparent resin to be in contact with an object under test, etc. In the light source module LM, a power supply section (not shown) controls a current value so that a light amount of the light emitting section can be maintained to be constant. The light source module LM is mounted while the window member is in contact with the object under test (transparent window B) from the +Z side.

Figure 5:
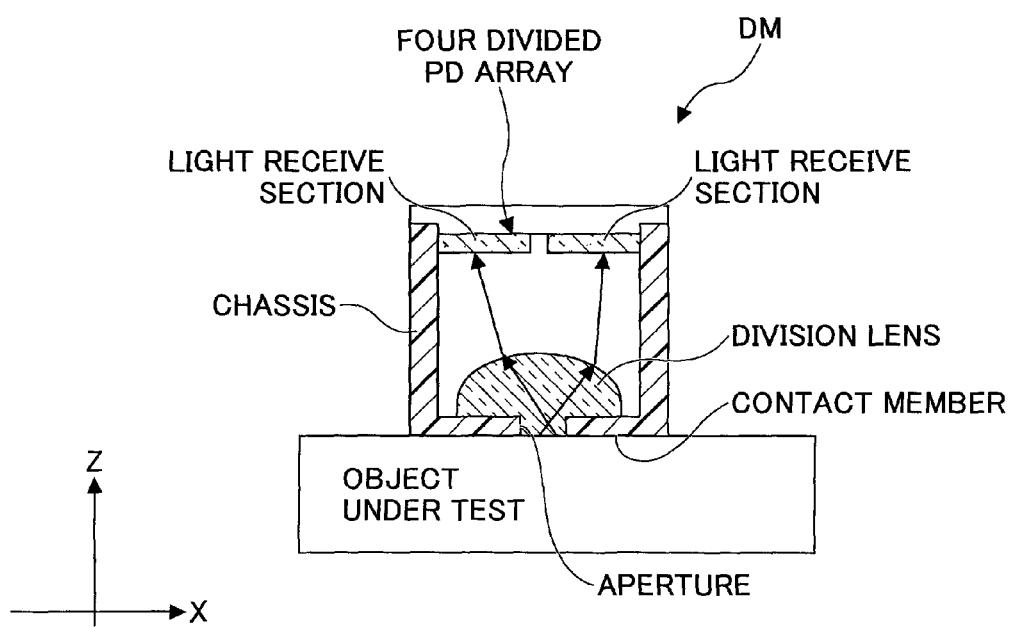
FIG. 5 is a drawing illustrating a schematic configuration of a detection module according to the example 1.

As illustrated in FIG. 5, the detection module DM includes a chassis made of a black resin, a contact member attached on the head of the chassis (at the edge on the −Z side) and made of an elastic body, a hemispherical lens (split lens) contained in the chassis and having a diameter of 3 mm, four divided photo diodes (four photo diodes (PDs) are arranged in an array manner), etc. Apertures (openings) are formed at the edge of the chassis and in the contact member. The detection module DM is mounted while the contact member is in contact with the object under test (transparent window A) from the +Z side. In FIG. 5, only two of four PDs (light receive sections) are illustrated.

The split lens is disposed on the +Z side of the aperture, so that the light, which is irradiated from the light source module LM and propagated in the object under test is incident on the split lens via the aperture, is refracted and emitted (transmitted) in the direction corresponding to the incident position and the incident angle into the split lens (see FIG. 5).

The four divided photo diodes are disposed on the +Z side of the split lens. The light passing through the split lens is incident on any one of the four light receive sections (PDs) in accordance with the traveling direction (emitting (transmitting) direction from the split lens). By doing this, in the detection module DM, it becomes possible to classify the light incident from the object under test into four angle ranges.

The control section detects light receiving amounts of the four light receive sections (PDs) of the detection modules DM mounted on the transparent windows A (i.e., in total the light receiving amounts of 16 PDs), converts the light receiving amounts into the respective voltage values by using operation amplifiers, and stores the voltage values in the recording section. The data are detected at a sampling rate of 1 ms, and the values measured for 20 s are averaged. In a single measurement, the data of 16 PDs are acquired.

Next, details of the light source module LM are described. The light source of the light source module LM employs a 40ch surface emitting laser array chip, that is, a surface emitting laser array chip having 40 Vertical Cavity Surface Emitting Lasers (VCSELs).

Figure 6:
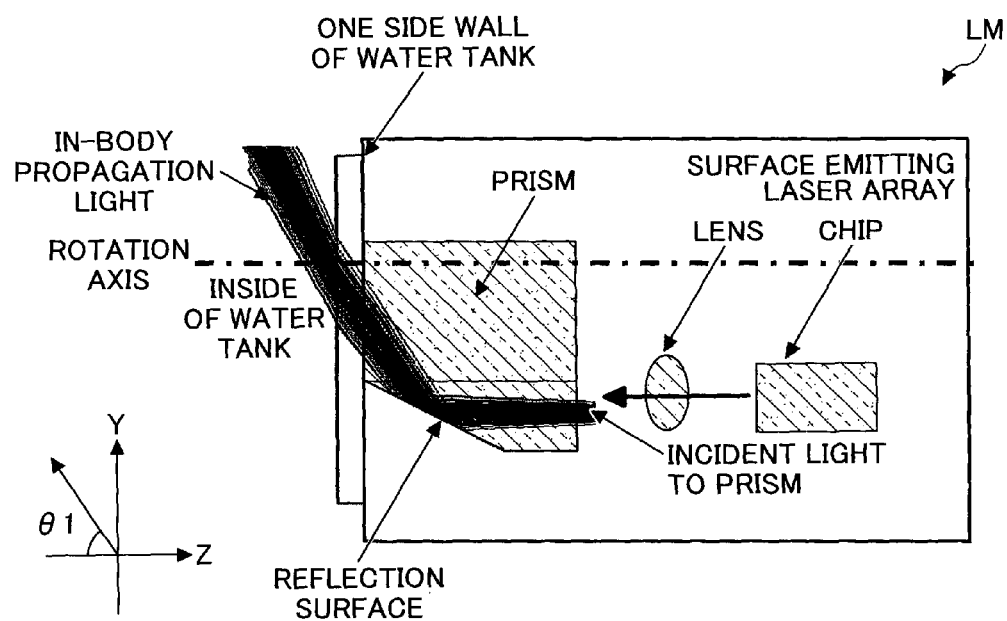
FIG. 6 is a second drawing illustrating a schematic configuration of the light source module according to the example 1.

On the light path from the surface emitting laser array chip, there is disposed a lens having a diameter of 3 mm so that the light substantially corresponds to the parallel light from the lens (see FIG. 6). The distance between the emitting surface (light emitting surface) of the surface emitting laser array chip and the main point of the lens (the optical center of the lens) is set to be equal to the focal length (distance) "f" (e.g., 9 mm). Namely, the surface emitting laser array chip is disposed so that the emitting surface is positioned at the position of the focal point of the lens. Here, the "focal length of the lens" refers to the distance between the main point and the focal point of the lens.

Here, the 40ch of the VCSEL simultaneously emit light and the total output at that time is approximately 50 W. The parallel light beams emitted from the VCSEL are refracted by the prism as illustrated in FIG. 6.

As the prism, an acrylic prism having the refractive index substantially equal to that of the acrylic water tank is employed (used). The reflecting surface of the prism is designed to fit the diameter of the prism, and the angle of the reflecting surface is set so that the light that passes through the lens is incident on the acrylic water tank with the incident angle of approximately 50 degrees.

A difference in refractive index between the acryl of the water tank and the prism and the phantom (i.e., the Intralipid water solution) is set so that the propagation angle in the phantom is approximately 60 degrees ("θ1" in FIG. 1) by Snell's law. The prism is installed on a rotation stage (not shown) which is provided on an inner wall of the water tank and is rotatable around a rotational axis extending in the Z axis direction.

Figure 7:
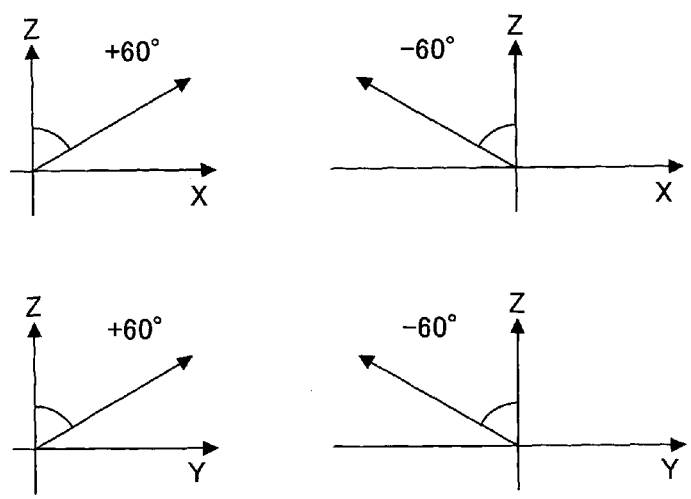
FIG. 7 is a drawing illustrating propagation angles in a living body.

By rotating the rotation stage together with the prism, it becomes possible to change the incident angle and orientation of light to the prism. Here, as illustrated in FIG. 7, four orientations (i.e., +X, −X, +Y, and −Y orientations) are sequentially measured. Namely, these four directions measurements are performed at each position of the four light source modules (B1 through B4), so that 16(=4×4) measurements are performed. Between the prism and the water tank, a gel resin (not shown) having the refractive index substantially equal to that of the prism and the water tank is filled (supplied). By having the gel resin, refraction and reflection can be prevented.

Next, a method of measuring the information in the object under test is described with reference to a flowchart in FIG. 8.

First, the probes are set (step T1). Here, as described above, the "probes" collectively refer to the detection module DM and the light source module LM. The probes to be set here are four detection modules DM and one light source module LM. Those four detection modules DM are mounted in the four transparent windows A having the diameter of 9 mm as illustrated in FIG. 3, respectively. One light source module LM is mounted in the transparent window B1 as illustrated in FIG. 3.

Next, the 40ch (light emitting sections) of the light source modules LM simultaneously emit light (step T2). The current value is determined so that the total emission intensity is approximately 50 mW. The light emitting time is approximately 20 s. During the light emitting time, the PD detection values of the four detection modules DM are read (step T3). Several points of the data detected every 1 ms interval (detection values) are averaged. Then, the averaged detection values (i.e., average values of the detection values) are stored in the recording section (step T4).

Here, the measurements are performed in the four orientations (i.e., +X direction, +Y direction, −X direction, and −Y direction) (four-direction measurement) (steps T5 and T6). Specifically, in steps T2 through T4 right after step T1, the measurement is performed while the prism is arranged in the +X direction. Next, the prism is rotated to be arranged in the +Y direction (step T6). In this state, steps T2 through T4 are performed. Next, the prism is rotated to be arranged in the −X direction (step T6). In this state, steps T2 through T4 are performed. Next, the prism is rotated to be arranged in the −Y direction (step T6). In this state, steps T2 through T4 are performed.

Next, the mounting position of the light module LM is sequentially changed from the transparent window B1 to the transparent windows B2, B3, and B4 in this order, so that the four-direction measurement is performed in each of the positions (steps T7 and T8). After that, the position of the light absorption body is moved and the four-direction measurement is performed in each of the four mounting positions of the four light source modules LM (steps T9 and T10).

In the stored data, the data when there is the light absorption body and the data when there is no light absorption body are given as: "r(s,i,n)(i=1, 2, 3, . . . , M, n=1, 2, 3, . . . , K)" and "r(0,i,n)(i=1, 2, 3, . . . , M, n=1, 2, 3, . . . , K)", respectively. Here, the "i" denotes numbers that are allocated to the respective detection modules DM. The "n" denotes numbers that are allocated to respective groups. Next, respective differences Δr(i,n) are calculated.

Figure 39:
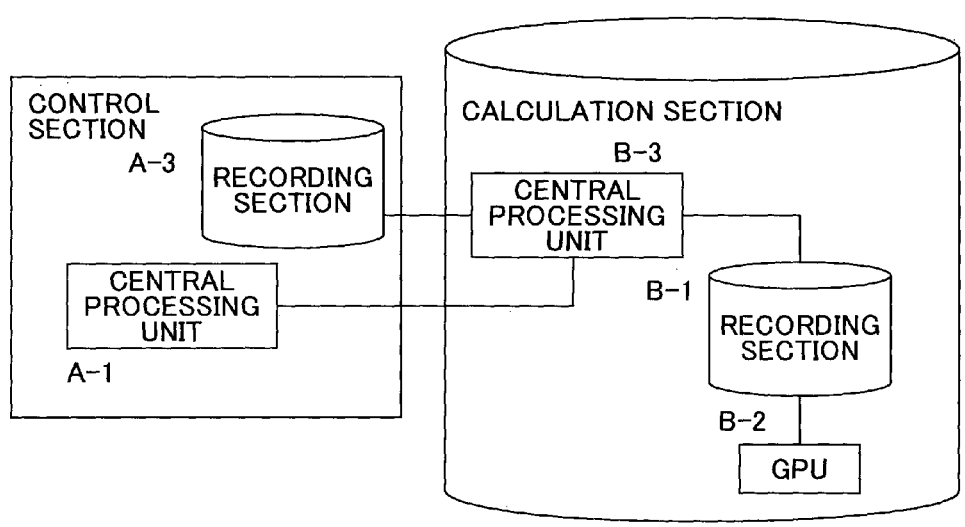
FIG. 39 is a block diagram illustrating a configuration of a calculation section.

In the following, a method is described of calculating the position of the light absorption body (optical characteristic of the pseudo living body) based on the measurement results acquired by the above-described measurement method based on the flowchart of FIG. 8. Here, an inverse problem estimation algorithm is used. In order to resolve the inverse problem, first, measurement and simulation (Monte Carlo simulation) are performed so that a sensitivity distribution is formed in a direct problem (see steps S21 through S25 in FIG. 9). FIG. 39 illustrates a block diagram of the calculation section. The information, which is to be used in the Monte Carlo simulation, indicating the positions of the modules (probes), the refractive index and the shape of the living body and the like are recorded in a recording section (B-1). Based on the information, the direct problem is performed. In the calculation, a multi-graphics processing unit (GPU) capable of parallel computing is used. By using the multi-graphics processing unit (GPU), the computing speed is much higher than that achieved in a conventional method. The sensitivity distribution acquired by the calculation is stored in the recording section (B-1) again. The calculation results and the measurement results stored in the recording section (A-3) are input to a Central Processing Unit (B-3), so that the central processing unit (B-3) performs inverse problem estimation. The estimation result is displayed on the display section via the Central Processing Unit (A-1) (see FIG. 38).

On the other hand, conventionally, it has been thought that in a scattering body such as a living body light is scattered substantially in an isotropic manner. However, even according to a recent scientific meeting and the like, it is reported that in a microscopic area in the order of millimeters, the light propagation is anisotropic. In order to perform simulation reflecting the anisotropy, it is necessary to use a transport equation or perform the Monte Carlo simulation.

In this embodiment, the emission light from the light source is deflected and incident in the object under test. Therefore, if a general diffusion equation is used, it is not possible to reflect the information of the incident angle. In this regard, a method of using a transport equation has been proposed. However, it is also known that it requires an immense amount of time to calculate using a transport equation.

Therefore, according to this embodiment, Monte Carlo simulation is employed. The Monte Carlo simulation refers to a method in which the conditions that photons are scattered in a scattering medium are stochastically expressed by using a random variable and the macroscopic behavior thereof are observed. Specifically, the behavior is modeled in a manner such that whenever photons in a medium move a predetermined distance, the photons collide with each other and the orientations (directions) thereof are changed. The average value of the "predetermined distance" is a mean free path defined by the scattering coefficient, and the change of the direction is defined by the anisotropy "g". How the collisions are repeated and how the photons propagate within a defined area are recorded. By calculating an infinite number of photons that are modeled as described above, it becomes possible to simulate the Monte Carlo simulation, what kind of path a single photon scatters along is recorded.

In the Monte Carlo simulation according to this embodiment, it is assumed that the number of the photons is $10^9$ and the voxel is a 1 mm cube, and the calculation for the three-dimensional area of 120 mm×120 mm×60 mm is performed. Here, the scattering coefficient, the absorption coefficient, the anisotropy, and the refractive index of the scattering medium are respectfully set as 7.8 mm$^{-1}$, 0.019 mm$^{-1}$, 0.89, and 1.37, which are substantially the same as those of human scalp. The phantom (i.e., the Intralipid water solution) having those values is prepared, and the simulation is performed under the same conditions of all the light source modules LM, the propagation angle, the positions of the detection modules DM and the like as those in the phantom to calculate the sensitivity distribution.

In this case, the number of photons that passed the voxel position "r" is defined as "$\varphi_0(r)$". Especially, when the position of the light source module LM is given as "rs", the photon pass number at the voxel position "r" is defined as "$\varphi_0(rs,r)$". Next, the light source module LM is disposed at the position where the detection module DM was disposed, and then, the number of the photons is calculated again. When the detection module was set at the position "rd", the number of the photons that passed the voxel position "r" is defined as "$\varphi_0(r, rd)$".

The light path is invertible. Due to this, the product is proportional to the number of the photons that have passed the voxel position "r", were emitted from the light source module LM, and have entered in the detection module DM. The product that is standardized by all the number of photons "$\varphi_0(rs, rd)$" that enter in the detection module DM is the following sensitivity distribution "A(r)"

$$A(r) = \frac{\phi_0(rs, r)\phi_0(r, rd)}{\phi_0(rs, rd)}$$

The sensitivity distribution "A(r)" denotes an influence rate on a detection amount at the position "r". That is, the sensitivity distribution "A(r)" indicates how much the detection amount is changed by an occurrence of the light absorption body at the voxel position "r".

Figure 10:
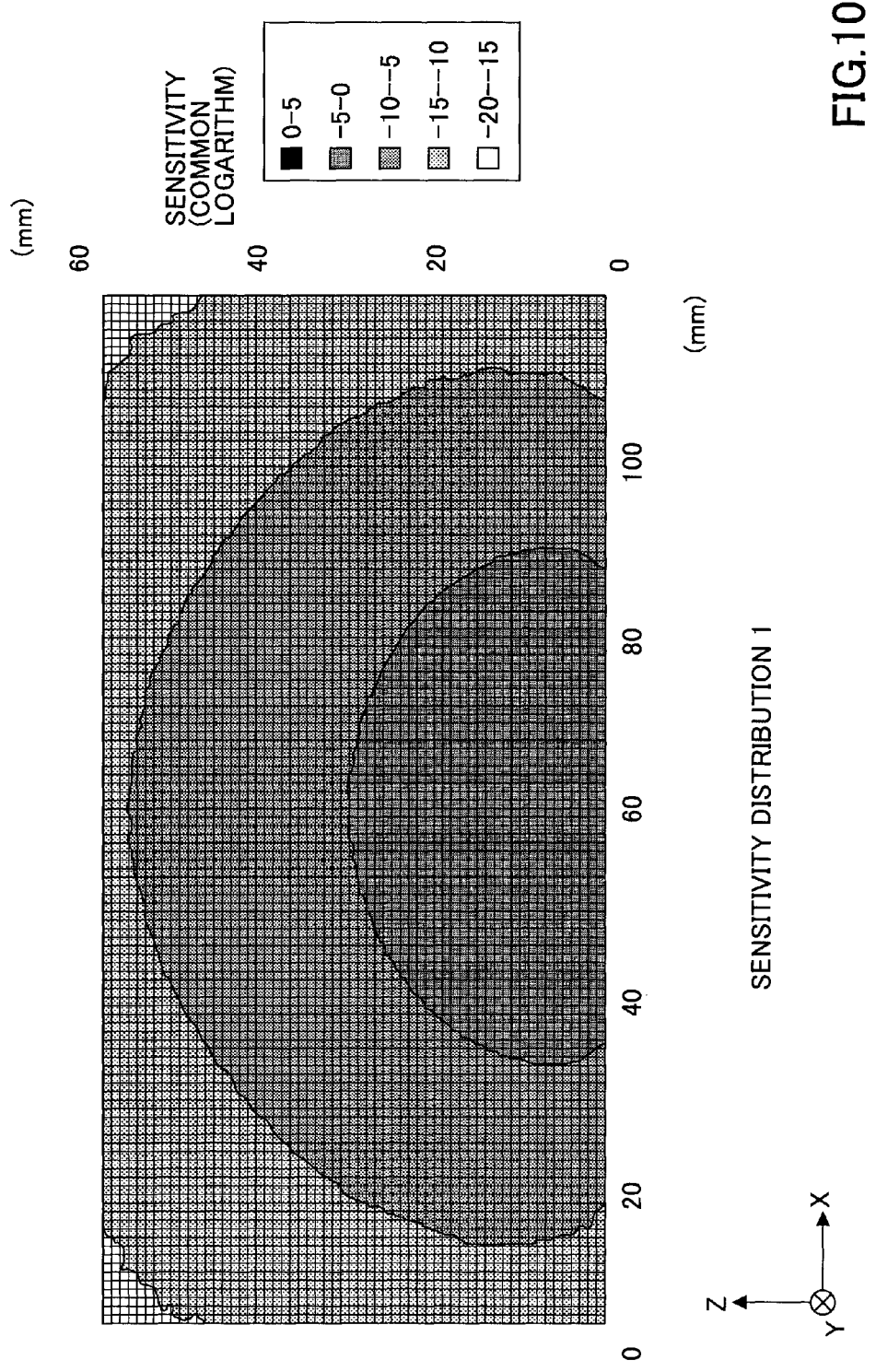
FIG. 10 is a first drawing indicating sensitivity distribution in a Photo Diode (PD)

FIG. 10 illustrates an example of the sensitivity distribution calculated as described above. In the example, the light source module LM and the detection module DM are arranged at the positions (X,Y,Z)=(45,60,0) and (X,Y,Z)=(75,60,0), respectively. The voxel is a 1 mm cube. Therefore, the voxel is equivalent to the unit (mm) of the values. The sensitivity of the voxel at those positions is expressed in the logarithm with a base of 10 (i.e., common logarithm).

Figure 11:
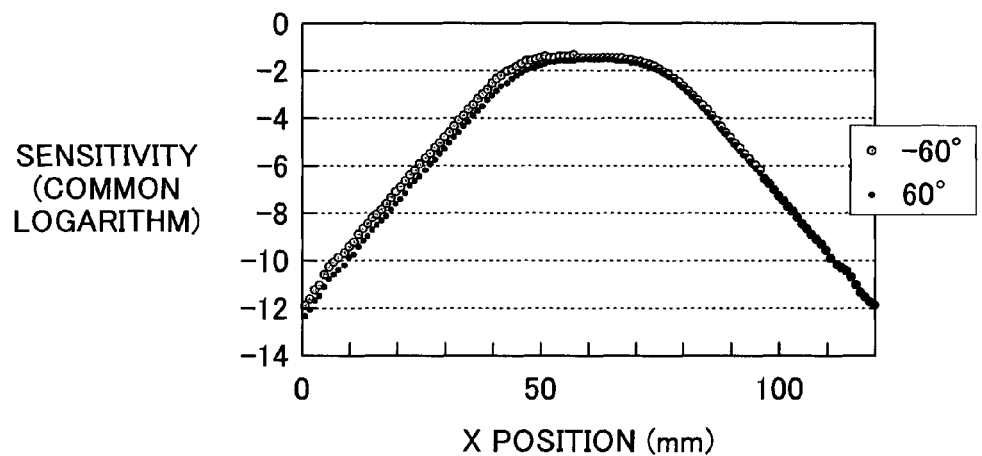
FIG. 11 is a second drawing indicating sensitivity distribution in a PD.
Figure 12:
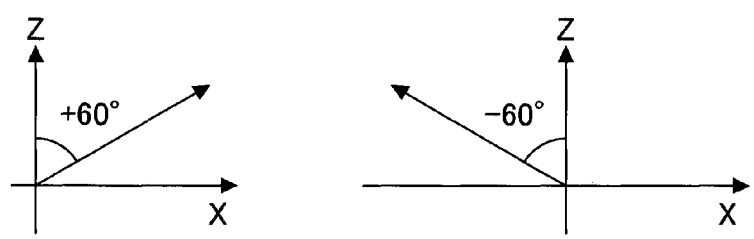
FIG. 12 a drawing illustrating propagation angles in a living body.

Next, FIG. 11 is a graph of a result of plotting the sensitivity (vertical axis) at the position "x" (lateral axis) on the line where Y=60 and Z=10 in the voxel (x, y, z). In this case, the results of the cases where the angles relative to the X axis as the propagation angle on the plane when the Y axis is regarded as the normal line are +60 degrees and −60 degrees are indicated in FIG. 12.

As illustrated in FIG. 11, there is a difference in the sensitivity distributions between the angle is +60 degrees and −60 degrees. This difference can be used as the index of whether it is possible to improve the resolution. Namely, the difference that occurred in the sensitivity distributions indicates that the light propagation paths from two light sources are different. This is because, if the light propagation paths from two light sources are the same, substantially the same sensitivity distributions should be obtained even when the propagation angle is changed. Because of the different light propagation paths from the two light sources, the light from the one of the two light sources collects information different from the information collected by the light from the other one of the two light sources.

This creates a great value for the inverse problem estimation described below. As described above, light does not scatter in a simple isotropic manner but does indicate slight anisotropy in several mm order. Due to the difference in such a several mm order, it becomes possible to realize the inverse problem estimation having a resolution in a several mm order. The sensitivity distribution is realized in all the propagation angle/detection angle conditions relative to all the combinations between the light source module and the detection module DM performed in the phantom.

Next, by using the sensitivity distribution, the inverse problem estimation is performed.

When it is assumed that the change of the absorption coefficient "$\Sigma\mu_a(r)$" caused by the existence of the light absorption body is sufficiently small, the following formula is obtained based on Retov (Rytov) approximation.

$$\log\frac{\phi_0(rs, rd)}{\phi(rs, rd)} = \frac{v}{S}\frac{\int d\vec{r}\phi_0(rs, r)\delta\mu_a(r)\phi_0(r, rd)}{\phi_0(rs, rd)}$$

Here, the symbol "v" denotes light speed in the medium, the symbol "S" denotes an amount of light emitted from the light source module per unit time, the symbol "rs" denotes the position of the light source module LM, the symbol "rd" denotes the position of the detection module DM, the symbol "$\varphi_0(rs, rd)$" denotes an amount of light emitted from the light source module LM and delivered to the detection module DM, and the symbol "$\varphi_0$" denotes the light intensity in a state where there exists no light absorption body. This formula teaches that when the light intensity "$\varphi_0$" is given in a state where there exists no light absorption body, it is possible to relate the change of the absorption coefficient "$\Sigma\mu_a(r)$" caused by the existence of the light absorption body to the observation value log φ(rs, rd) by a linear relationship.

When it is simply described, the following formula can be used.

$$Y = A(r)X$$

Here, the symbol "Y" denotes the change of the observation value depending on whether there exists a light absorption body or not, and the symbol "X" denotes the change of the absorption coefficient at the voxel position "r".

The Symbol "A(r)" denotes the sensitivity distribution. Based on the above formula, it becomes possible to understand how the observation value changes when the position and the amount of the light absorption body, which are expressed by "X", are changed.

In the inverse problem estimation, the reverse process is performed. Namely, the position "X" of the light absorption body is estimated by using the observation value "Y". As described in the above position measurement method, the measurement is performed by assuming that the change depending on whether there exists a light absorption body is expressed as Δr(i,n). This Δr(i,n) corresponds to the observation value "Y", so that the position "X" is calculated based on the observation value "Y".

Generally, an estimation method for an inverse problem called "L2-norm normalization" is used. In this method, the "X" that minimizes the following cost function C is calculated.

$$C = |Y - AX|^2 + \lambda|X^2|$$

Here, the symbol "Y" denotes the observation value, the symbol "A" denotes the sensitivity distribution, and the symbol "λ" denotes a normalization coefficient. In an inverse problem, such method is generally used. However, in this embodiment, as the inverse problem estimation, a Bayesian estimation in which detection in the depth direction is possible is used. Details of the inverse problem estimation using the Bayesian estimation are described in the following Non-Patent Document: T. Shimokawa, T. Kosaka, O. Yamashita, N. Hiroe, T. Amita, Y. Inoue, and M. Sato, "Hierarchical Bayesian estimation improves depth accuracy and spatial resolution of diffuse optical tomography," Opt. Express *20*, 20427-20446 (2012).

Figure 13A:
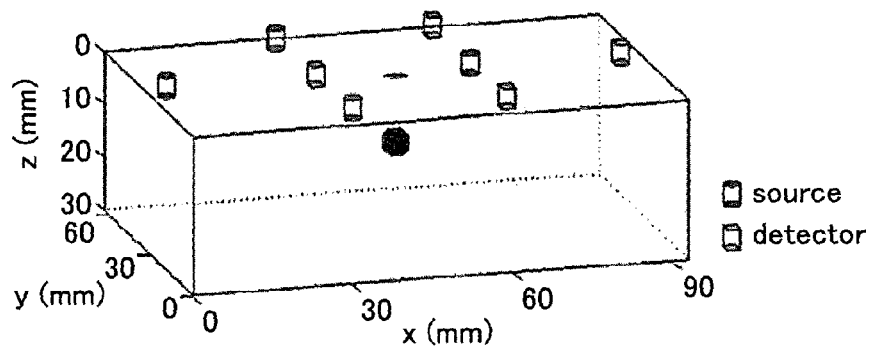
FIG. 13A is a drawing illustrating an actual position of a light absorption body.
Figure 13B:
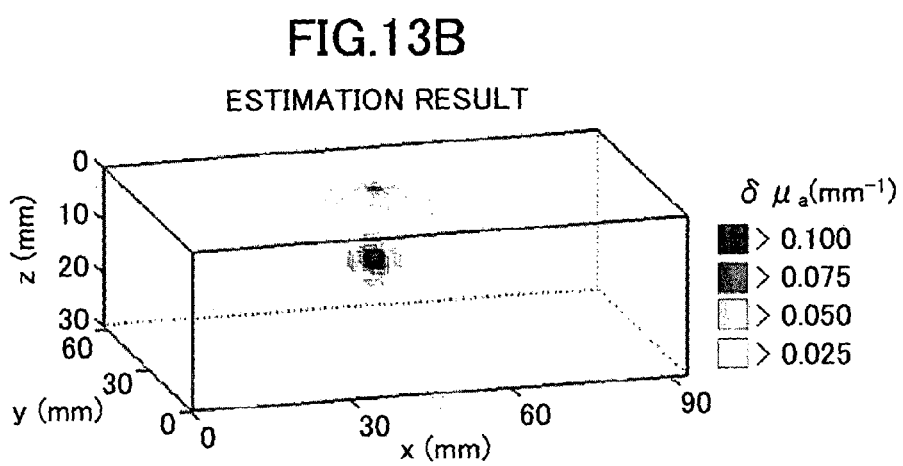
FIG. 13B is a drawing illustrating an estimation result of the position of the light absorption body.

As a result, it becomes possible to acquire the estimation result as illustrated in FIG. 13B. FIG. 13A illustrates the position of the light absorption body. The grid of FIG. 13B is 3 mm, so that it is understood that the estimation result corresponds to the actual position under the accuracy of 3 mm.

Figure 13C:
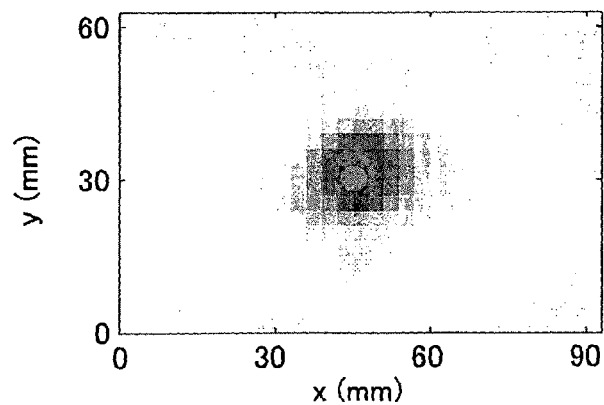
FIG. 13C is a drawing illustrating an estimation result of the position of the light absorption body in a comparative example.

As a comparative example, FIG. 13C illustrates a result when only one direction among the four directions is used for the detection. The configuration in this comparative example is substantially the same as that in a conventional NIRS (DOT) device. In this comparative example, the detection in the depth direction is not possible, and the detection result is extremely expanded. In the example 1, due to the Bayesian estimation, it becomes possible to detect the position and the depth of the light absorption body.

Figure 14A:
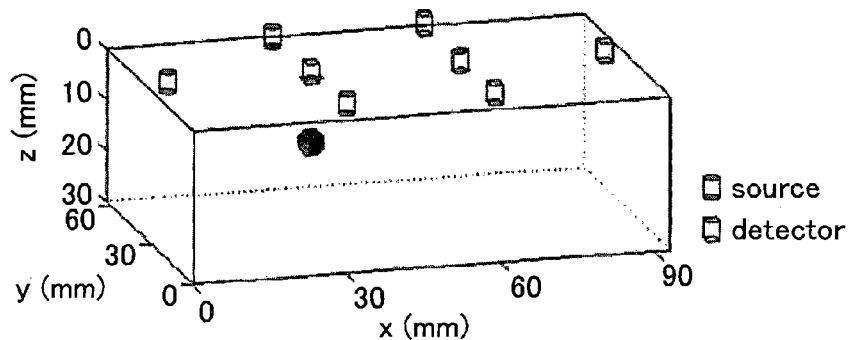
FIG. 14A is a drawing illustrating an actual position of a light absorption body after movement.
Figure 14B:
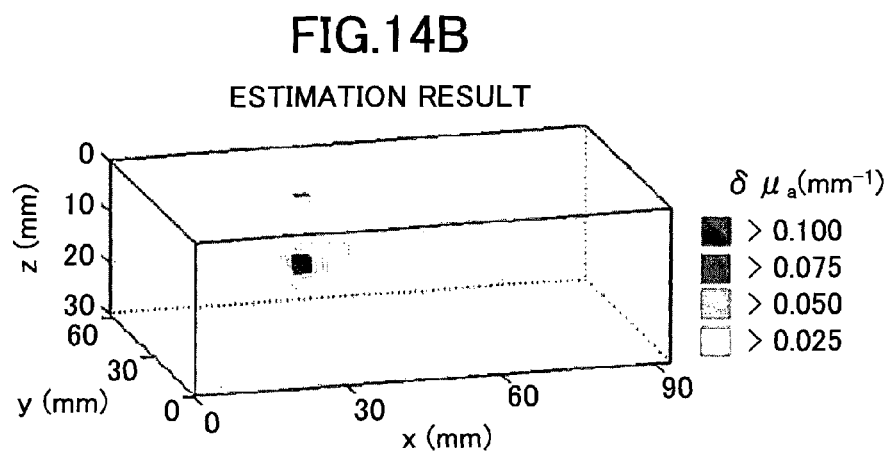
FIG. 14B is a drawing illustrating an estimation result of the position of the light absorption body after movement.
Figure 14C:
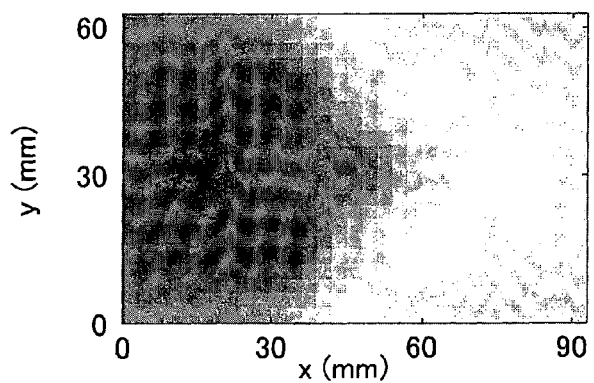
FIG. 14C is a drawing illustrating an estimation result of the position of the light absorption body in a comparative example.

Further, after the position of the light absorption body is changed (see FIG. 14A), the estimation is performed. The estimation result is illustrated in FIG. 14B. In this case as well, it is understood that the actual position of the light absorption body can be accurately estimated. By employing the method of example 1, it become possible to detect the position of the light absorption body with higher resolution. On the other hand, in the comparative example, as illustrated in FIG. 14C, the detection result of the light absorption body is expanded, and it is not possible to accurately detect the position of the light absorption body.

In the following, an example 2 in this embodiment is described. In the description of example 2, parts related to example 1 as well are also described.

Example 2

First, black ink is dropped in the Intralipid water solution (diluted Intralipid 10% concentration with water) having filled an acrylic water tank so that the black ink is approximately 200 ppm so as to obtain the absorption coefficient and the scattering coefficient which are substantially the same as those of a living body. Then, a light absorption body having black color which simulates blood flow is dipped into in the white Intralipid water solution. Here, it is assumed that the light absorption body is a black spherical object made of polyacetal and having a diameter of approximately 5 mm. In order to control the position of the spherical object, the spherical object is fixed to a thin metal bar having a diameter of 1 mm connected to an automatic stage. The positions of the probes on the transparent windows are accurately determined, so that the probes are attached to the transparent windows. For example, the acrylic water tank has a cuboid figure so that the volume (size) of the acrylic water tank is 140 mm×140 mm×60 mm and the thickness of the wall of the acrylic water tank is 1 mm.

The optical sensor 10 includes an irradiation system having plural (e.g., eight) light source modules LM and a detection system having plural (e.g., eight) detection modules DM. The plural light source modules LM and the plural detection modules DM are connected to the control section via electronic wiring.

The control section controls the light emitting timings of the light source modules LM and the detection timings of the detection modules DM, and transmits the acquired detection results to the recording section. Further, the control section performs control so as to read the data recorded in the recording section, performs calculations using values in the data, and displays the calculation results on the display section.

Figure 15:
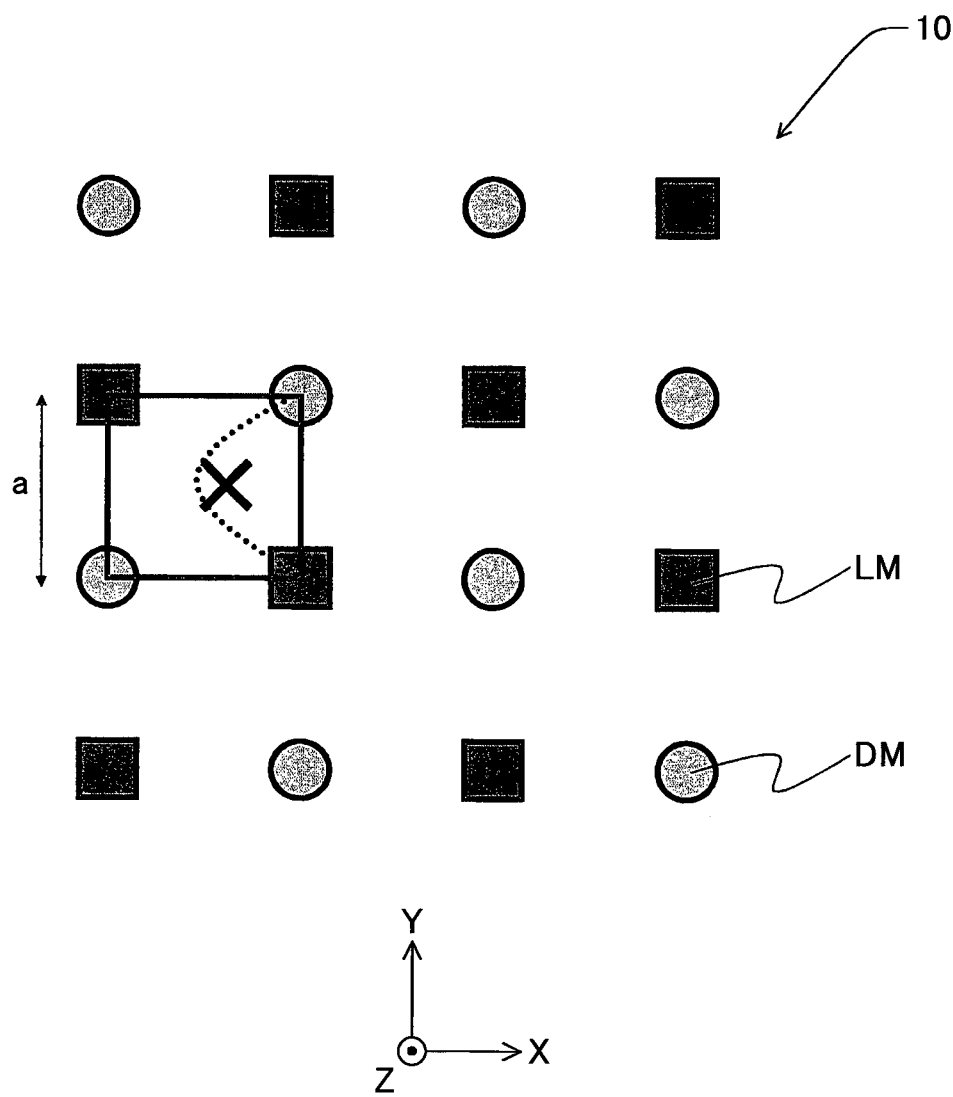
FIG. 15 is a drawing illustrating layout of plural light source modules and plural detection modules in an optical sensor according to a second embodiment.

As illustrated in FIG. 15, for example, eight light source modules LM and eight detection modules DM are disposed in a matrix manner (two-dimensional lattice manner) so that the light source module LM and the detection module DM are disposed next to each other at a constant pitch "a" in both X direction and Y direction, which are orthogonal to each other, relative to the pseudo living body (not shown). In FIG. 15, the light source modules LM are expressed by using a square mark and the detection modules DM are expressed by using a circular mark.

Figure 16:
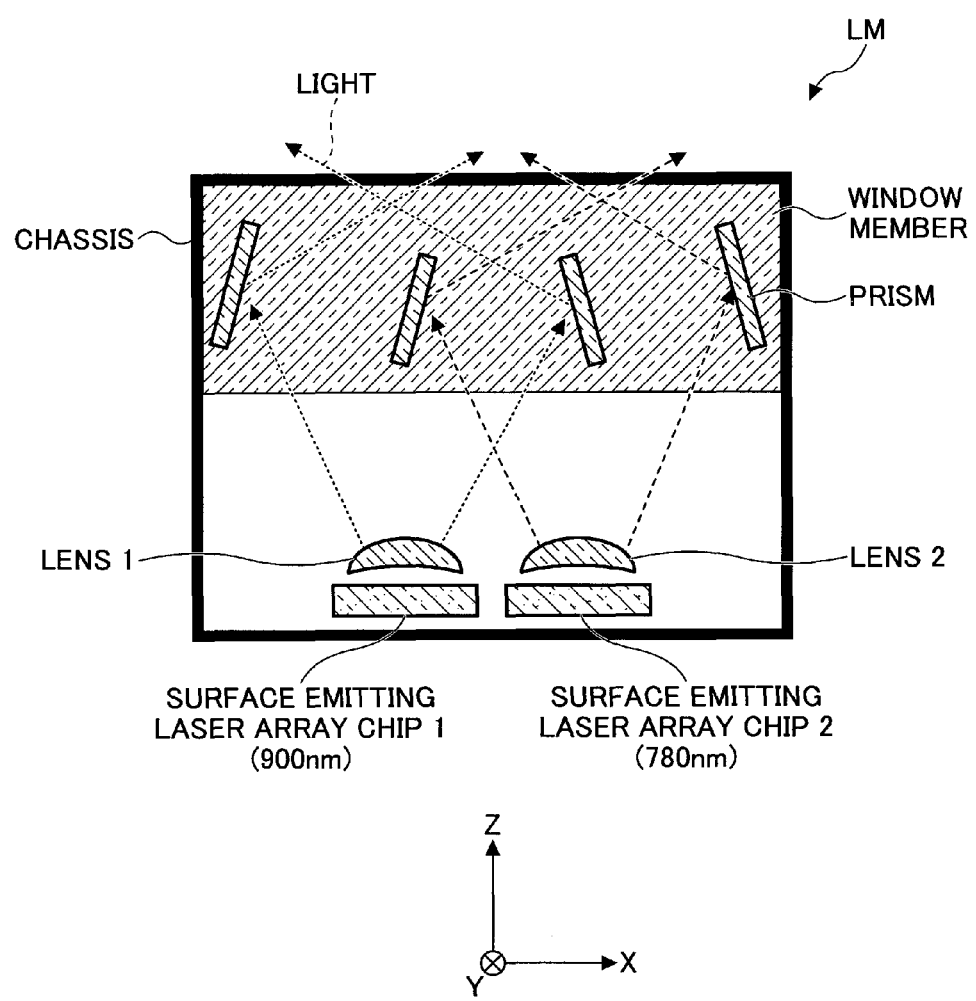
FIG. 16 is a first drawing illustrating a schematic configuration of a light source module according to an example 2.

As illustrated in FIG. 16, the light source module LM includes, for example, optical elements such as lenses and prisms, a ceramic package (not shown) on which plural surface emitting laser array chips are mounted, a flexible printed circuit board (not shown) on which the ceramic package and an analog electronic circuit are mounted, wirings and connector sections (not shown) connected to the flexible printed circuit board, a chassis containing those elements, a window member made of a transparent resin to be in contact with an object under test, etc.

The oscillation wavelength of the Vertical Cavity Surface Emitting Lasers (VCSELs) of the surface emitting laser array is, for example, 780 nm or 900 nm. Those wavelengths are selected because the absorption coefficient greatly changes in the oxygen concentration in blood. As illustrated in FIG. 16, in the light source module LM, a surface emitting laser array chip 1 having the oscillation wavelength of 900 nm and a surface emitting laser array chip 2 having the oscillation wavelength of 780 nm are disposed side by side, and a lens 1 is disposed near the emitting end of the surface emitting laser array chip 1 and a lens 2 is disposed near the emitting end of the surface emitting laser array chip 2. The surface emitting laser array may also be called "ch (channel)".

The light beams from the surface emitting laser array chips are refracted by the respective lenses and deflected to the desired angle (reflected to the desired direction) by the prisms, as reflection members, which are formed in the window member.

Figure 17:
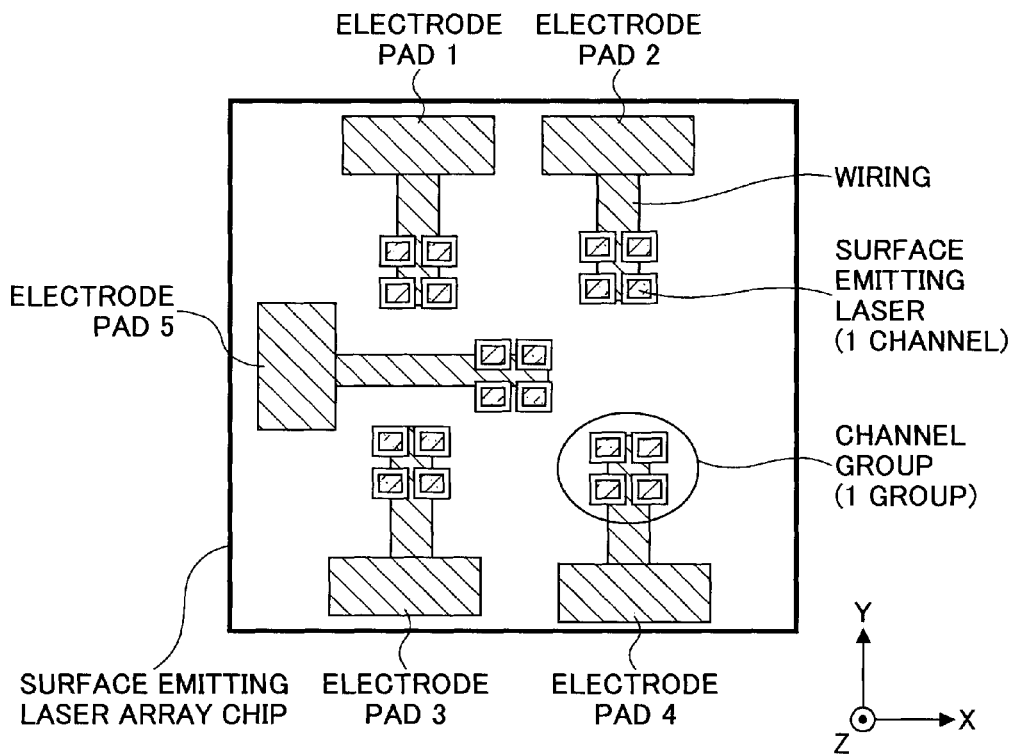
FIG. 17 is a drawing illustrating a surface emitting laser array chip.

As illustrated in FIG. 17, the surface emitting laser array chip has a square shape having a side of approximately 1 mm, and includes plural (e.g., 20) surface emitting lasers.

In more detail, each surface emitting laser array chip has five groups (ch groups), each group having four surface emitting lasers. Here, the centers of four groups among the five groups are disposed at the respective corners of the square and the center of the rest of one group is disposed at the center of the square.

The four channels in each group are mounted in the ceramic package and are connected to the same electrode pad (one of electrode pads 1 through 4) via bonding wiring (a wired line).

The ceramic package is mounted on a wiring pattern of the flexible printed circuit board by soldering. On the flexible printed circuit board, are a semiconductor circuit for switching and a semiconductor circuit for stabilizing current. The semiconductor circuit for switching controls the surface emitting laser array chip which of the channels emits light. The semiconductor circuit for switching causes the selected channel to emit light based on an external serial signal. One end of the signal line for the serial signal and one end of the a power supply line are connected to the flexible printed circuit board, and the other end of the signal line for the serial signal and the other end of the power supply line are connected to the control section.

The amount of emitted light of each channel is periodically set to be constant by calibration. In a usual use method, the five groups are sequentially emitted using short pulses. In such a pulsed light emission, it is possible to prevent a temperature increase due to the heat generation and accordingly it is adapted to stabilize the amount of emitted light. The detection values, which are acquired by the detection module whenever the light is emitted based on the short pulses, are accumulated and averaged. By doing this, the influence of noise can be reduced.

In the following, why the surface emitting laser array chip is employed as the optical sensor 10 light is described. In the surface emitting laser array chip, it is possible to arrange plural channels at the positions close to each other in a two dimensional manner, and it is also possible to independently control the light emission of those channels. Further, it is possible to change the traveling directions of the emitted light beams by disposing lenses near the channels.

Further, in the optical sensor used in the DOT, it is desired to accurately control the incident angle to the object under test as much as possible. The emission angle of a general-purpose light-emitting diode (LED) is large. Due to this, in order to acquire accurate parallel light, it is necessary for the lens to have an aspheric surface. Further, the emission angle of a general-purpose light-emitting diode (LED) is asymmetric. Due to this, in order to acquire accurate parallel light using a lens, it is necessary to combine a lens having the curvature in the vertical direction different from the curvature in the lateral direction and a cylindrical lens. Namely, the configuration becomes complicated and a highly-accurate mounting technique is required.

On the other hand, the surface emitting laser has a substantially exact circular shaped far field pattern. Due to this, parallel light can be acquired by disposing one spherical lens. When coherent light emitted from the LD is used, speckle, in which scattered light beams interfere with each other, occurs in an object under test (scattering body). The speckle pattern negatively affects the measurement as noise.

When blood flow in a brain is observed by such as the DOT, the scattering number is extremely large. Therefore, the negative influence is limited. However, there is an influence of returned light in which the light reflected by a skin surface directly returns to the light source. The returned light makes the oscillation state in the LD unstable, so that a stable operation cannot be performed. In a case of an optical disk, in order to stably use the coherent light, a wave plate is used to prevent the normally reflected light from becoming the returned light. However, it is difficult to remove the returned light related to the scattering body.

In the case of the surface emitting laser array chip, it is possible to simultaneously irradiate plural light beams to a fine area. Also, it is possible to reduce the interference caused by the returned light (see, for example, Japanese Laid-open Patent Publication No. 2012-127937).

Figure 18:
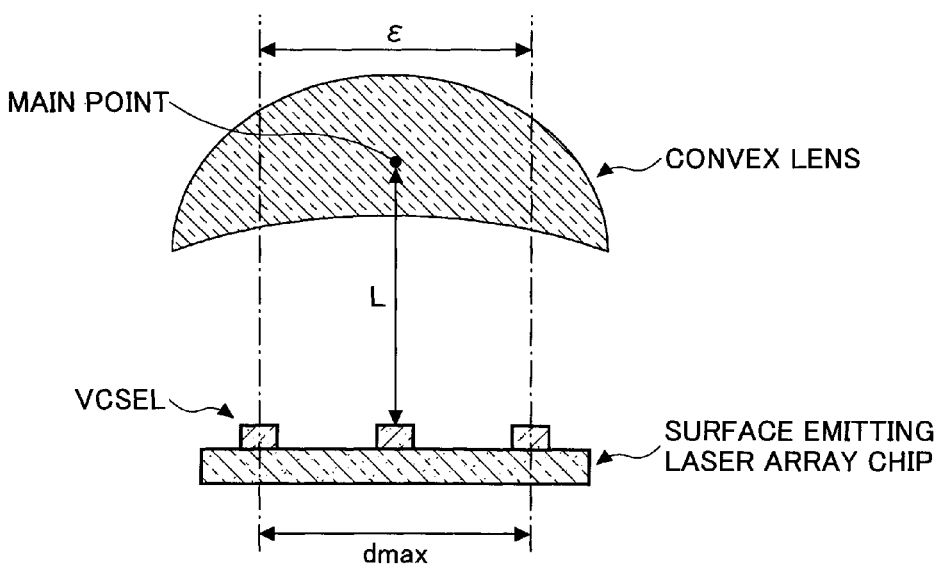
FIG. 18 is a second drawing illustrating a schematic configuration of a light source module according to the first embodiment.

In this embodiment (examples 1 and 2), there is a convex lens (hereinafter may be simplified as a "lens") disposed on an optical path of the light from the surface emitting laser array chip (see FIG. 18).

The diameter of the convex lens is 1 mm, and the effective diameter "ε" of the convex lens is 600 μm. The focal length of the convex lens is 600 μm. The surface emitting laser array chip is a 1 mm×1 mm chip. A distance between the centers of the two channels which are separated most in the surface emitting laser array chip "dmax" is 600 μm. By setting the effective diameter "ε" and the distance "dmax" to be equal to each other, it becomes possible to minimize the diameter of the convex lens.

Here, the positions of the convex lens and the surface emitting laser array chip are determined in a manner such that the distance "L" between the main point (optical center) of the convex lens and the light emitting surface (emitting surface) of the surface emitting laser array chip in the optical axis direction of the convex lens is, for example, 300 μm (i.e., f≠L).

In this case, the light emitted from the surface emitting laser array chip and having passed through the convex lens is normally reflected by the prism or the like, so that it becomes possible to avoid the occurrence of a phenomenon that the light is collected on the surface emitting laser array chip by the convex lens (returned light phenomenon). As described above, the returned light does not occur. Therefore, it becomes possible to stabilize the amount of light emitted by each of the channels in the surface emitting laser array chip.

However, when the influence of the returned light is not considered (when higher resolution is not necessary in the NIRS), it is possible to set f=L.

Figure 19:
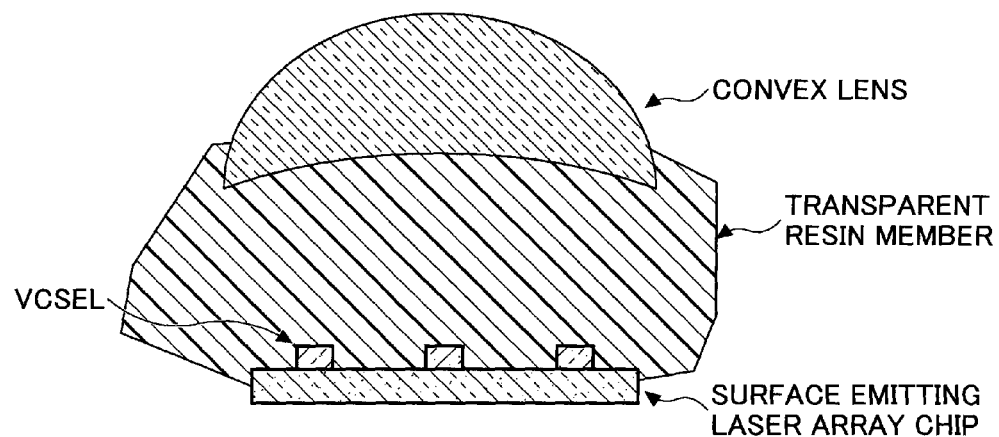
FIG. 19 is a third drawing illustrating a schematic configuration of a light source module according to the first embodiment.

Further, as illustrated in FIG. 19, a transparent resin may fill in between the convex lens and the surface emitting laser array chip, so that no air layer is formed therebetween. As the transparent resin, a resin having the refractive index similar to that of the convex lens (e.g., thermosetting epoxy-based resin) is used. Namely, the refractive index does not change at the boundary surfaces between the convex lens and the surface emitting laser array chip. The transparent resin may be formed by metallic molding before fixing the convex lens or may be injected after fixing the convex lens.

As described, by supplying the transparent resin to fill in between the convex lens and the surface emitting laser array chip, it becomes possible to prevent the light, which is emitted from the surface emitting laser array chip, from being reflected by the surface on the surface emitting laser array chip of the convex lens. Namely, it becomes possible to prevent the occurrence of the returned light. Since the returned light does not occur, it becomes possible to stabilize the amount of light emitted from each of the channels. When the amount of light from each of the channels is stabilized, it becomes possible to increase the signal/noise (S/N) ratio of the measurement system, so that highly accurate NIRS measurement and the higher resolution can be realized.

Figure 20:
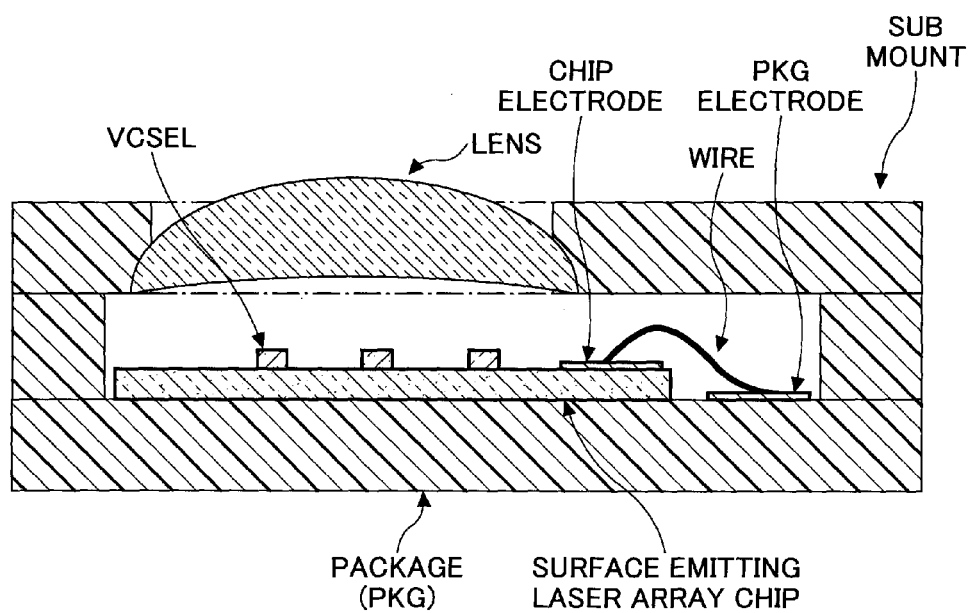
FIG. 20 is a fourth drawing illustrating a schematic configuration of a light source module according to the first embodiment.

As illustrated in FIG. 20, the convex lens is fixed to a package, on which the surface emitting laser array chip is mounted, via a sub mount. An electrode on the surface emitting laser array chip (chip electrode) is electrically connected to a PKG electrode on the package via a wire. The height of the wire is several tens μm, therefore, the wire is designed so as not to be interfered with the sub mount. The fixed position "L" of the convex lens (the distance between the light emitting surface of the surface emitting laser array chip and the main point of the convex lens) is limited by the height of the wire. Namely, when a wire is used, it is necessary to avoid the sub mount and set the height of the wire less than or equal to 100 μm. In other words, it is preferable that the relationship −100 μm<f−L<0 is satisfied. However, note that the transparent resin in FIG. 19 is omitted in FIG. 20.

The light emitted from the emitting surface of the surface emitting laser has a substantially circular shape, and the divergence angle is 5 degrees by the half-value width. Generally, the beam of the LD has an elliptical shape. Therefore, it is necessary to consider a setting error in the rotational direction. However, it is not necessary for the surface emitting laser to consider the setting error. Therefore, the surface emitting laser has merit. Further, due to the circular shape when an inverse problem is resolved using optical simulation, it becomes easier to use an approximation based on the symmetric property, which is another merit.

The beam emitted from the surface emitting laser is refracted by the convex lens disposed near the surface emitting laser. The refraction angle is determined based on the relational position between the surface emitting laser and the lens center (optical axis of the lens). In this regard, by setting the channels of the surface emitting laser array chip and the lens at the respective appropriate positions, it becomes possible to acquire a desired refraction angle.

In example 2, the relational position between the channels and the optical axis of the convex lens is determined so that the refraction angle is approximately 20 degrees. In the surface emitting laser array chip, it is possible to independently control the emissions of the channels. Therefore, by selecting the channel for the emission, it becomes possible to change the direction of light emitted from the light source module LM.

Figure 21:
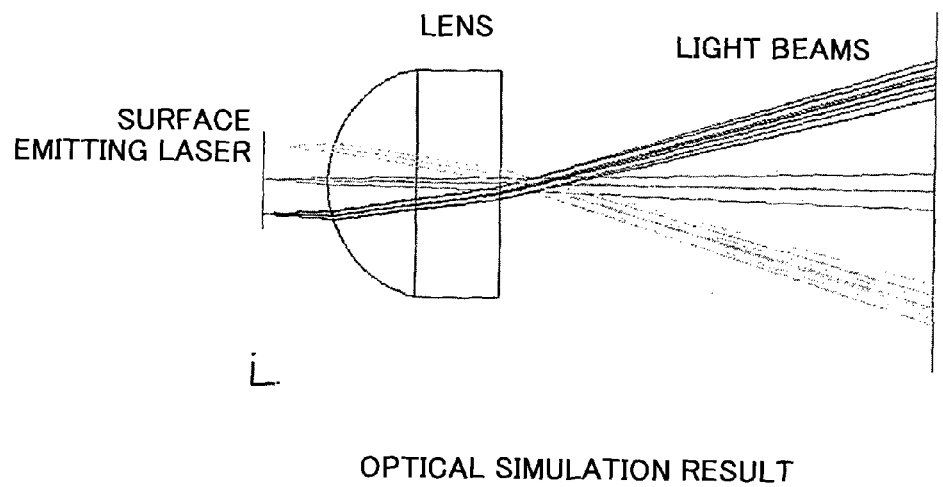
FIG. 21 is a light ray drawing optically designed by an optical simulator.

FIG. 21 illustrates an example of a light beam drawing optically designed by an optical simulator. Here, there are disposed three channels (light sources), which simulate the surface emitting laser array chip, and a lens (diameter 1 mm and f=600 μm) near the channels. One of the three channels is disposed on the optical axis of the lens. One of the other two channels is disposed on one side of the optical axis of the lens, and the other of the other two channels is disposed on the other side of the optical axis of the lens. The light from the channels other than the channel on the optical axis is refracted, so that the propagation direction (path) is bent. Namely, the two light beams, which are emitted from the channels other than the channel on the optical axis, are emitted in the directions opposite to each other and at the angle of approximately 20 degrees relative to the optical axis of the lens.

Here, the light source module LM is designed so that the incident angle of the light on the object under test is approximately 55 degrees. Specifically, as illustrated in FIG. 16, the light source module LM is designed so that, by individually deflecting the plural light beams, which are emitted from the convex lens in the directions inclined by approximately 20 degrees relative to the optical axis of the convex lens, in the directions inclined by approximately 55 degrees from the approximately 20 degrees relative to the optical axis of the convex lens by the plural prisms, the deflected light beams inclined by approximately 55 degrees can be incident on the surface of the object under test.

Figure 22:
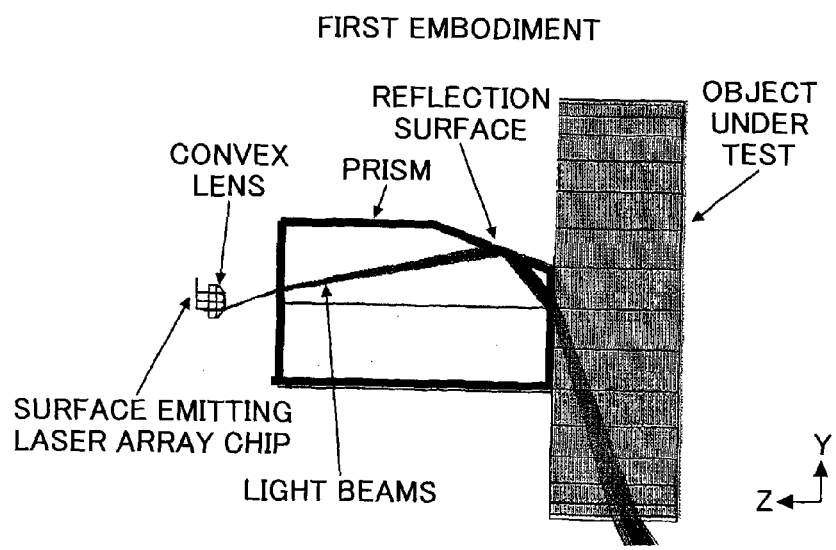
FIG. 22 is a drawing illustrating a result of optical simulation according to the first embodiment.

Here, as for the prism, it is necessary to reflect light. In this regard, for example, a glass substrate on which a metal membrane is formed may be used as the prism. Otherwise, for example, a prism using a total reflection phenomenon caused by a difference between refractive indexes may be employed. As one example of the prism, FIG. 22 illustrates a result of optical simulation. The light beams emitted from the VCSEL are refracted by the convex lens and incident on the prism.

Here, it is assumed that the material of the prism is BK7. However, a general-purpose optical material may be used. The light beams incident on the prism are totally reflected by the prism side surface (reflection surface), so that the reflected light beams can be incident on the object under test at the incident angle of approximately 55 degrees. In other words, the light beams having passed through the convex lens are deflected by the prism so that the incident angle of the light beams to the object under test becomes approximately 55 degrees. In this case, in order to prevent the light from being scattered in the boundary surface between the prism and the object under test, a transparent gel is placed between the prism and the object under test. Here, plural light beams from the surface emitting laser array chip are refracted into non-parallel light beams by the convex lens, so that the non-parallel light beams are reflected by the prism to be incident on the object under test. As a result, non-parallel plural substantially parallel light beams are incident on the same position of the object under test (see FIG. 22).

By Snell's law based on a difference in refractive index between the prism and the object under test, the propagation angle of the light beams in the object under test is changed from approximately 55 degrees to approximately 60 degrees.

In the optical system including the convex lens and the prism, by using a fact that the positions of the channels in the surface emitting laser array chip are different from each other, it becomes possible to set the propagation angle of the light beams in the object under test. Here, by separating the centers of the channels (VCSEL) from the optical axis of the convex lens by approximately 200 μm, it becomes possible to set the propagation angle of the light beams emitted from the channels to approximately 60 degrees in the object under test. In this case, the plural light beams emitted from the plural channels are emitted from plural different positions on the emission surface of the convex lens as non-parallel plural substantially parallel light beams.

Figure 23:
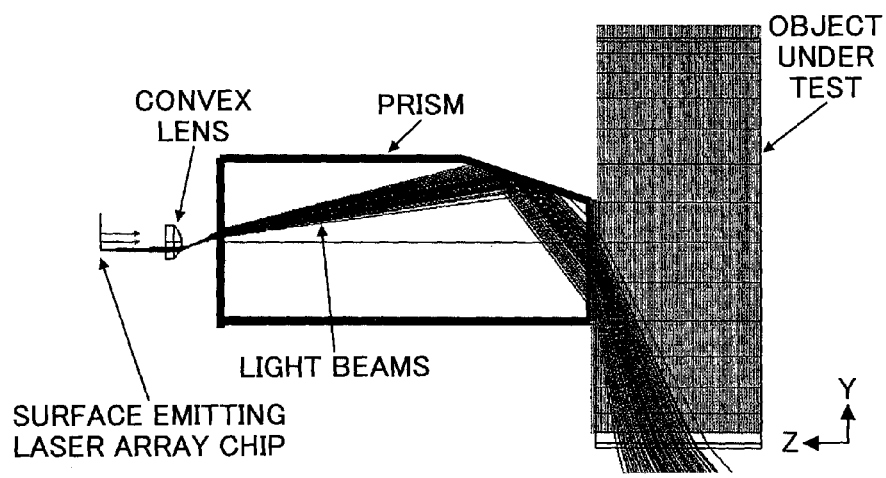
FIG. 23 a drawing illustrating a result of optical simulation according to a comparative example.

As a comparative example, FIG. 23 illustrates an optical simulation result in the case where the focal length "f" and the fixed position "L" of the convex lens are 600 μm and 1.6 mm, respectively. When the difference between "f" and "L" is greater than or equal to 1 mm, the light beams widely expand. When the light beams expand like this, it becomes necessary to enlarge the incident surface of the object under test. However, as the practical size of the incident surface in actual NIRS, the diameter of approximately 2 mm is the limit. This limit relates to a fact that the distance between adjacent human hair roots is approximately 2 mm. Namely, if the area is greater than this, it is not optically possible to realize the NIRS with higher resolution because of hair. In this regard, it is desired that the difference between "f" and "L" is less than 1 mm.

The lenses 1 and 2 in FIG. 16 are directly fixed to the ceramic package on which the surface emitting laser array chip is mounted so as to be accurately and stably disposed at the designed positions.

In FIG. 21, a case is described where the convex surface of the lens faces the surface emitting laser side. However, the convex surface of the lens may face the side opposite to the surface emitting laser side. As illustrated in FIG. 21, by disposing the convex lens in a manner such that the convex surface of the convex lens faces the surface emitting laser side and the plane surface of the convex lens faces the object under test side, the distance between the surface emitting laser array chip and the convex lens can be longer. In a process of mounting the chip, in order to avoid interference among parts and an arm for picking up the parts, it is preferable that the distance is longer to some extent.

As the lens, an optical part that refracts light may be used. For example, a Gradient index (GRIN) lens using the refraction index distribution of an optical fiber, etc., may be used. Generally, by using the GRIN lens, it becomes possible to select a lens having a smaller spherical aberration and the f value at lower cost.

In example 2, it is preferable that the spherical aberration is smaller so that the light is incident on an end part of the lens rather than the center part of the lens.

As described above, plural light beams that are non-parallel to each other are emitted from the light source module LM (see FIGS. 16 and 22).

Further, the plural light beams that are non-parallel to each other from the light source module LM are incident on the same position of the object under test (see FIGS. 16 and 22).

The term "same position" herein refers to the same position relative to the distance (e.g., approximately 60 mm) by which the light source modules LM are arranged (e.g., at the interval of approximately 60 mm). Therefore, plural positions separated from each other by several mm are included in the meaning of the "same position". In this regard, the term "same" in the "same position" is not the strict meaning of the "same". Therefore, the term "same" may be replaced by the term "substantially same" or "roughly same".

An algorithm to resolve the inverse problem is described below. In the algorithm, an optical simulation setting the position of the light source module LM is performed. In the optical simulation, by accurately setting the displacement of the incident position on the object under test, no error occurs in the inverse problem estimation. This also applies to the surface emitting laser array chip having plural channels having different oscillation wavelengths, so that even if the incident positions of the plural light beams from the plural channels having different oscillation wavelengths are separated by several mm, it is possible to say that the incident positions of the plural light beams are the same position.

However, as described in, for example, Patent Document 1, in order to dispose the probes in a high-density manner while the positions of the probes are separated from each other by 10 mm or more, it is necessary to independently dispose the plural light source modules. The operation to dispose the plurality of light source modules is complicated and is similar to the operation of putting hair aside one by one, so that the more the number of the light source modules increase, the more the number of the operations increase.

In this embodiment, as described below, by disposing only one light source module LM, it becomes possible to acquire an information amount the same as that acquired when plural light modules are disposed and it becomes possible to detect with higher resolution than is realized in the high-density probe as described in Patent Document 1 without increasing the complicated operations.

Figure 24A:
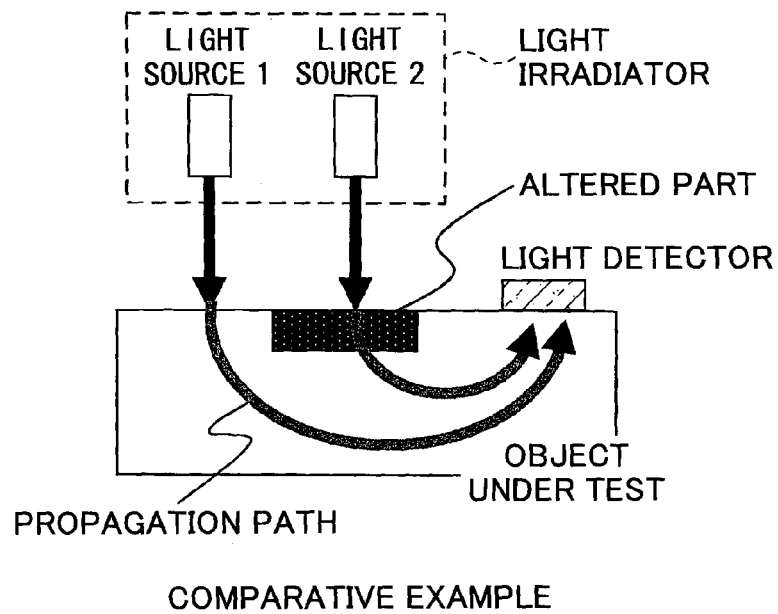
FIG. 24A is a drawing illustrating an operation of an optical sensor according to a comparative example.

Further, in a light source module according to a comparative example in which plural light beams which are parallel to each other are incident on a living body as illustrated in FIG. 24A, if there exists an altered part near the surface of the living body, a detection error may occur. The term "altered part" herein refers to a part whose optical characteristics are particular. The "altered part" includes, for example, a hair and artificially-colored skin. If there exists such an altered part, in this comparative example, the light from the light source 1 is incident at a position different from the position where the light from the light source 2 is incident, so that, for example, only the light from the light source 2 passes through the altered part. As a result, when the difference between the light source 1 and the light source 2 is calculated, the altered part becomes noise.

Figure 24B:
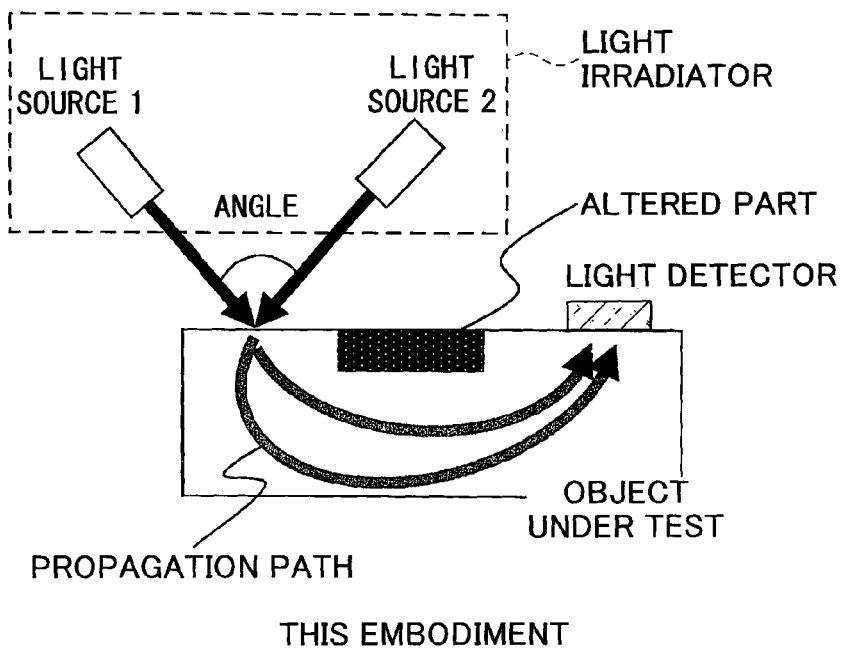
FIG. 24B is a drawing illustrating an operation of an optical sensor according to the first embodiment.

On the other hand, in this embodiment, as illustrated in FIG. 24B, the light from the light source 1 and the light from the light source 2 pass through the "same position" on the surface of the skin. Therefore, if the light from one of the light source 1 and the light source 2 passes through an altered part, the light from the other of the light source 1 and the light source 2 also passes through the altered part. Similarly, if the light from one of the light source 1 and the light source 2 does not pass through an altered part, the light from the other of the light source 1 and the light source 2 does not pass through the altered part, either. More specifically, both the light from the light source 1 and the light from the light source 2 take the same light path near the skin surface, and take the different light paths in the depth direction. Namely, it is not very sensitive to detect a difference near a skin surface, but it is sensitive to detect a difference near brain tissue. By reducing the noise near the skin surface, the resolution is improved. As described above, the meaning of the term "same position" permits the displacement of several mm.

Further, in example 2, a transparent gel is dropped onto the window member formed in the chassis, so that the transparent gel is placed between the window member and the surface of the object under test to prevent air being introduced therebetween.

In a conventional light source module, the light, which is first irradiated into the air, is incident on and propagates in a body via the skin surface. In this case, a difference in refractive indexes is generated between the air having the refractive index of 1.0 and the living body having the refractive index of 1.37. Due to the generated difference in the refractive indexes, reflection and scattering occur. Further, the refractive index of the living body where light propagates is less than that of air outside the living body. Therefore, the propagation angle in the living body (hereinafter may be referred to as a "in-body propagation angle") relative to the incident angle becomes smaller. The light refraction at a boundary surface can be understood when Snell's formula is used. Snell's formula can be expressed by using the refractive indexes only.

Figure 25:
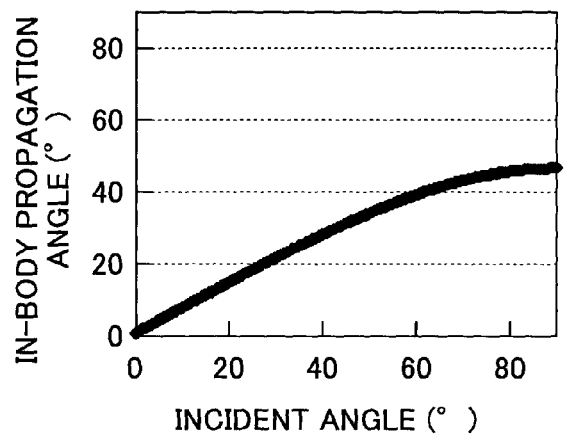
FIG. 25 is a graph illustrating a relationship between an incident angle from air to a living body and a living body propagation angle.

FIG. 25 is a graph illustrating the relationship between the incident angle and the in-body propagation angle at the boundary surface between the air (incident side: the refractive index is 1.0) and the living body (propagation side: the refractive index is 1.37). As understood from FIG. 25, even when the incident angle of the light incident on the living body is 60 degrees, the propagation angle of the light in the living body becomes 40 degrees which is smaller than the incident angle. Due to this, it is understood that, if it is necessary to achieve the propagation angle of the light in the living body greater than or equal to 60 degrees, it is not possible to achieve such propagation angle when the light is incident from air. In other words, it is difficult to achieve a large propagation angle of light in the living body if the light is first emitted in air.

Figure 26:
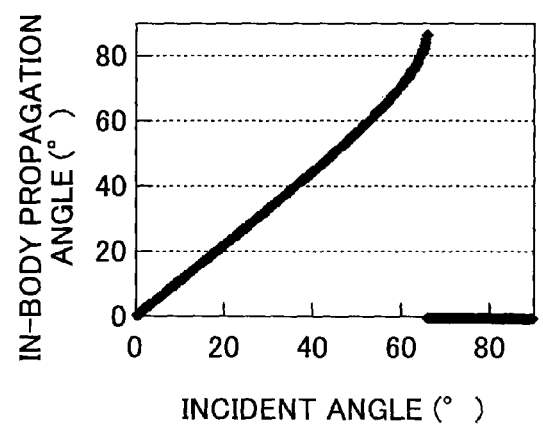
FIG. 26 is a graph illustrating a relationship between an incident angle from resin to a living body and a living body propagation angle.

To resolve the problem, in example 2, the refractive index of the transparent resin which is the material of the window member of the light source module LM is set to be greater (e.g., 1.5 or greater) than the refractive index (1.37) of the living body (see FIG. 26). In this case, the propagation angle in the living body of the light, which is directly incident on the living body from the light source module LM at the incident angle of 60 degrees, exceeds 70 degrees. In designing the light source module LM, when the angle is reduced, it becomes possible to obtain advantages such as reducing the size of the light source module LM.

In the light source module LM in example 2 having a configuration as described above, as illustrated in FIG. 16, the light, which is emitted from the surface emitting laser in the direction parallel to the optical axis of the lens, is refracted by the lens and travels in the direction included by approximately 20 degrees relative to the optical axis of the lens to be incident on the window member. Here, the refractive index of the window member is approximately 1.5. The light having passed through the lens is refracted when the light is incident on the window member. However, because the incident angle is not deep, the refraction is not great. The light, which is incident on the window member, is deflected by the reflection surface of the prism and travels in the direction included by approximately 55 degrees relative to the optical axis of the lens. This angle of 55 degrees is the angle in the window member having the refractive index of 1.5. However, as illustrated in FIG. 26, the propagation angle in the living body (refractive index: 1.37) becomes approximately 60 degrees.

In order for the light from the light source module LM to be directly incident to propagate in a pseudo living body, it is necessary to remove an air layer in the boundary surface between the pseudo living body and the light source module LM. The transparent gel selected here is a glycerin solution that is compatible with the pseudo living body. Due to volatile characteristics, the transparent gel is prepared so as not to be volatilized during testing (i.e., while the light source module is capped) and so as to be volatilized at an appropriate timing after testing or absorbed into the pseudo living body. Further, the optical characteristic of the transparent gel is prepared so as to be transparent when the wavelength is approximately 480 nm and so that the refractive index of the transparent gel is similar to that of a pseudo living body surface. Here, the refractive index of the transparent gel is prepared to have the value of approximately 1.37. By preparing in this way, even when the pseudo living body surface is uneven, a difference in the refractive index due to the uneven surface is not generated so that it becomes possible to produce a state where no reflection occurs. Accordingly, it becomes possible to remove most reflections at the pseudo living body surface. Further, even when the boundary surface with the pseudo living body is physically uneven, it is not optically uneven. Therefore, no scattering occurs. As a result, it becomes possible to accurately propagate the light in the pseudo living body in an appropriate propagation direction in accordance with the emission angle of the light from the light source module LM. Generally, scattering strongly occurs due to the propagation in the pseudo living body. However, scattering at the skin surface is not weak. Due to this, it becomes possible to secure high anisotropy of the light. Since a high anisotropy can be acquired, it becomes possible to greatly change the incident angles of the plural light beams from the light source module LM onto the pseudo living body, and as described below, it becomes possible to greatly change the incident angles of the plural light beams received by the detection module DM.

Figure 27:
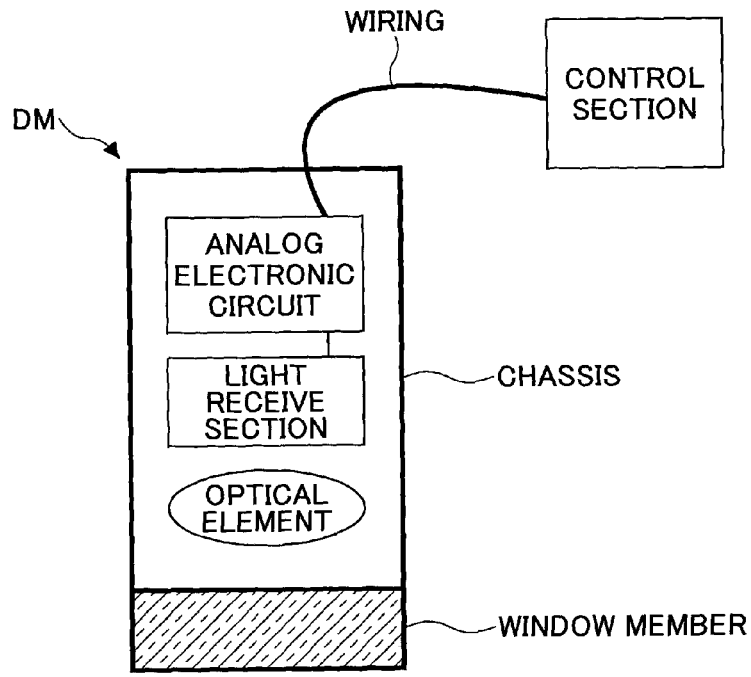
FIG. 27 is a first diagram illustrating a schematic configuration of a detection module according to the example 2.

As illustrated in FIG. 27, the detection module DM includes a chassis, an optical element, a flexible printed circuit board (not shown) including light receive sections and an analog electronic circuit, wirings and connector sections (not shown) connected to the flexible printed circuit board, etc.

Figure 28:
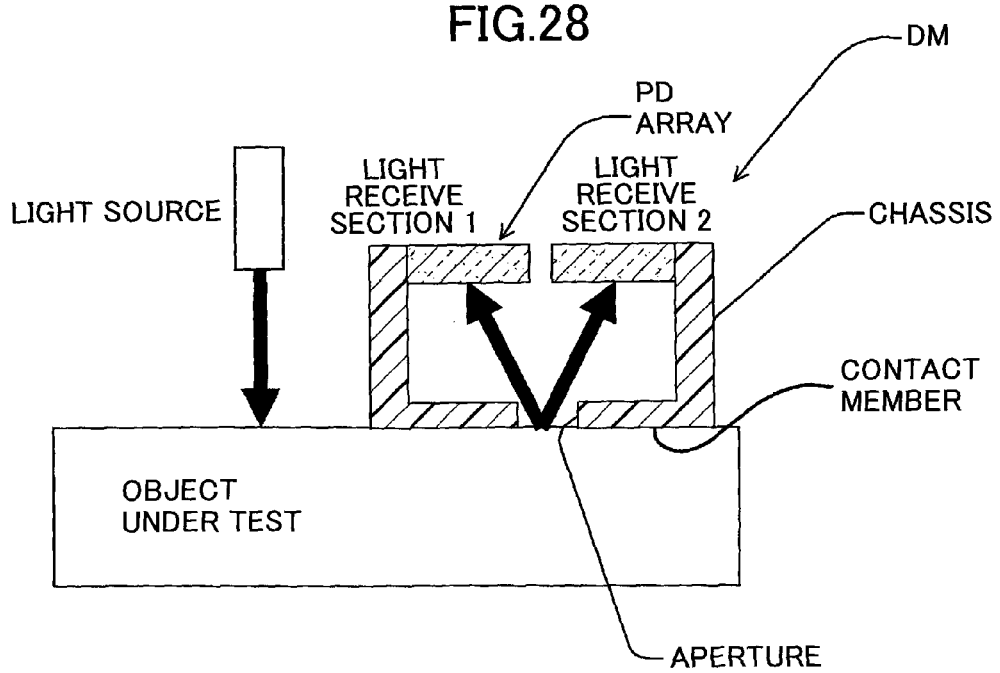
FIG. 28 is a second diagram illustrating a schematic configuration of the detection module according to the example 2.

As illustrated in FIG. 28, in the light detection module DM, the light, which is irradiated from the light source onto a pseudo living body and propagates in the pseudo living body, is divided into plural light beams to be guided into plural light receiving sections.

In a related art technology (see Japanese Laid-open Patent Publication No. 2011-179903), in a DOT using fluorescent light, the light receive sections are arranged so as to correspond to the plural light beams emitted at plural angles from the object under test. However, when the light receive sections are arranged in this way, the light incident on the light receive sections corresponds to all the emission angles from the object under test.

On the other hand, the detection module DM in this embodiment divides the light from the "same position" of the object under test and separately detects the divided light. Here, as described above in the light source module LM, since it is possible to design it in the optical simulation, the accuracy of the "same position" does not matter if the position differs in several mm order.

Figure 29:
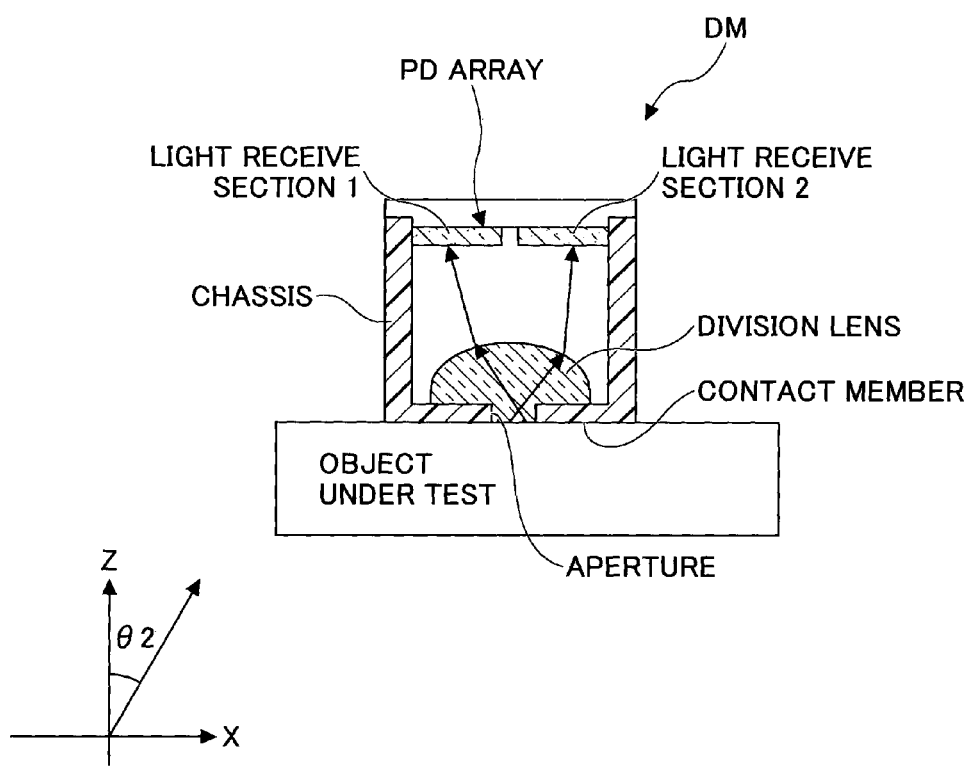
FIG. 29 is a third diagram illustrating a schematic configuration of the detection module according to the example 2.

In the following, details of the detection module DM are described. As illustrated in FIG. 29, the detection module DM includes a chassis made of a black resin, a contact member attached to the top end of the chassis and made of an elastic member, a transparent division lens contained in the chassis, and four light receive sections. An aperture (opening) is formed at the top end of the chassis and the contact member.

As the contact member, a member made of black rubber is used to enhance the light-blocking effect. From the aperture of the contact member, the center part (having a diameter of approximately 1 mm) of the division lens protrudes by several hundreds μm outside beyond the chassis. This protruded part is in contact with the living body surface. Therefore, optically there is no air and, for example, Fresnel refraction and scattering are reduced.

Further, in the detection module DM as well, the transparent gel is used because the stability can be further improved. The division lens is made of a transparent resin and has a refractive index of approximately 1.8. The division lens is fixed to the chassis.

The aperture is a circular hole having a diameter of approximately 1 mm and penetrating through the top end of the chassis and the contact member, so that the aperture has a function to limit positions where the light, which propagates in the object under test, is output from the object under test. The light output from the position is directed in different plural directions. Therefore, it becomes possible to limit the incident position of the light by the aperture, and then, the incident light is divided into plural light beams with the division lens, so that the plural light beams can be separately detected.

The above feature that the light from the object under test is incident onto the light receive section from the "same position" is realized by the aperture.

The light having passed through the aperture is refracted by the division lens to different directions corresponding to the propagation directions of the light. Therefore, the incident positions on the light receive sections differ.

The division lens is a spherical lens having a diameter of approximately 3 mm and a focal length "f" of approximately 3 mm.

In example 2, the division number of the light by the division lens is four. In response to this, a photo diode array (PD array) having four light receive sections (photodiode PD) arranged in two dimensional manner is used. In FIG. 29, however, only two light receive sections 1 and 2 of the four light receive sections (PDs) are illustrated.

Here, the PD array has a square shape whose one side length is approximately 3 mm, and each PD has a square shape whose one side length is 1.4 mm. The angle "θ2" is defined as illustrated in FIG. 29, and the distance between the PD array and the aperture is approximately 5 mm.

One surface of the lens is plane surface, and only the other surface is a spherical surface. The plane surface side of the lens is in contact with the pseudo living body. The position of the aperture is displaced from the focus position of the lens. Therefore it is not possible to create parallel light. However, the aperture has a function to limit the light to be incident on the PD array.

According to an optical simulation performed on this optical system, it is understood that the light having the angle "θ2" in a range of approximately −10 degrees to 50 degrees is incident on the light receive section 2 and the light having the angle "θ2" in a range of approximately −50 degrees to 10 degrees is incident on the light receive section 1. Namely, the light, which propagates in the pseudo living body and is emitted from the aperture, is divided into plural light beams depending on the emission angles and each of the plural light beams is incident on any one of the four light receive sections.

In example 2, a case is described where the spherical lens is used as the division lens. However, for example, an aspherical lens may be used so as to detect at larger angles. The division accuracy and the division number have a correlation with the estimation accuracy of the inverse problem described below. Therefore a necessary optical system is determined based on the desired estimation accuracy. In this embodiment, the spherical lens and the division number "4" are employed.

Each of the PDs is electrically wired to be connected to an operational amplifier. As the operational amplifier, a semiconductor operational amplifier is used to supply a power voltage of 5 V. The amount of the detected light is very small. Therefore, the gain of the operational amplifier is high and a two-stage amplifier configuration is employed. In the first stage, magnifications of tens of thousand times are performed, and in the second stage, magnifications of thousands of times are performed.

Figure 30:
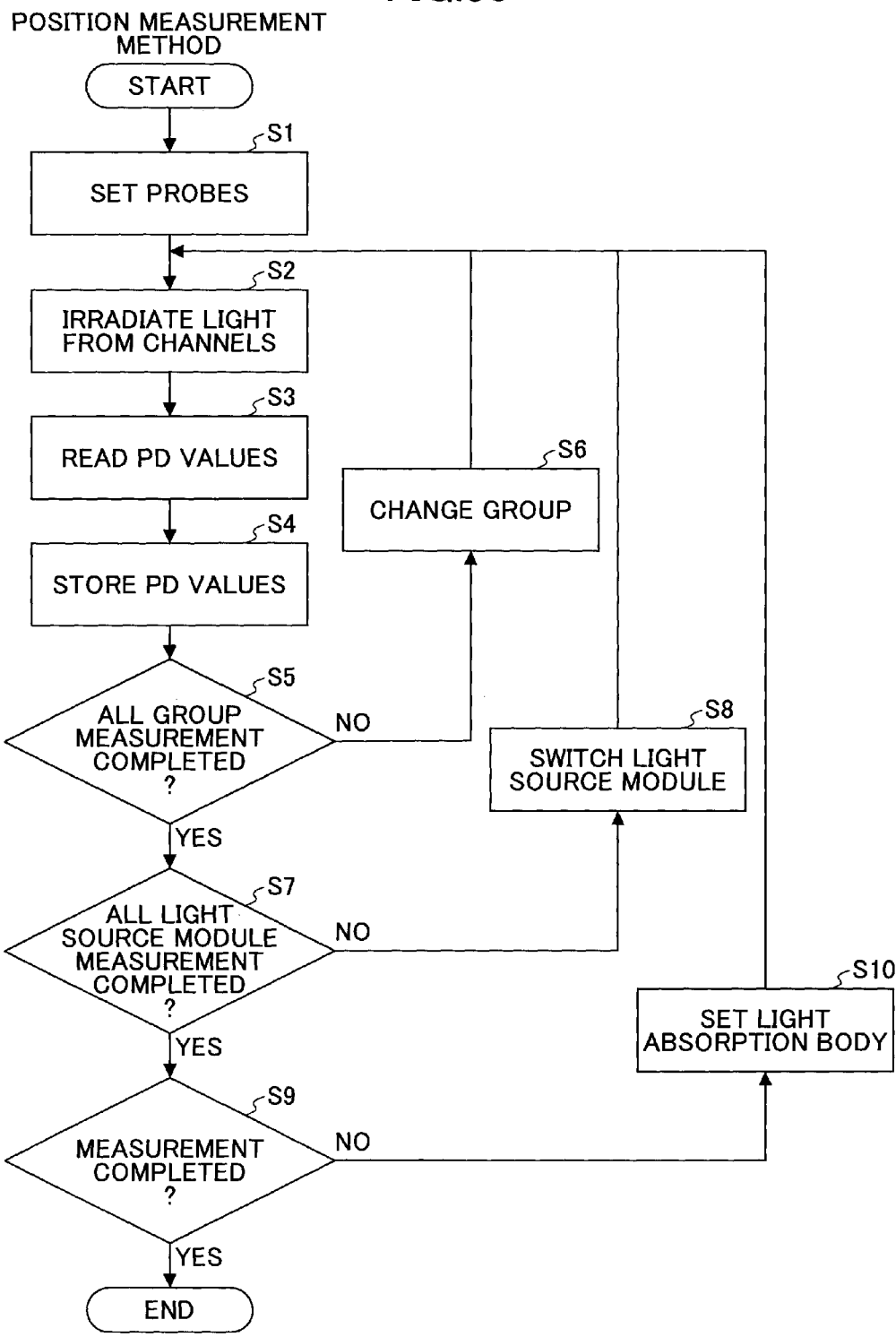
FIG. 30 is a flowchart of an optical characteristic detection method (position measurement method) according to the example 2.

In example 2, a method (position measurement method) of measuring the position of the light absorption body in the pseudo living body (an optical characteristic detection method of the object under test) is described with reference to a flowchart in FIG. 30.

First, the probes (the light source modules LM and the detection modules DM) are set on (attached to) the pseudo living body (step S1). In this case, a transparent gel is placed between the acrylic water tank and the probes and the probes are carefully set at the positions determined by the fixing members one by one so as not to generate air bubbles in the transparent gel.

The probes are eight light source modules LM and eight detection modules DM (total 16 probes). The light source modules LM and the detection modules DM are disposed next to each other at a constant pitch in a lattice manner (see FIG. 15). The lattice pitch (between lattice points) is 30 mm. The distance between the light source module LM and the detection module DM is 30 mm.

In this state, an arbitrary one light source module DM emit (step S2). The emission is performed on a group (4 channels) basis, and the current value is determined so that the emission intensity is approximately 4 mW. The emission time period is approximately 10 ms. During that time period, the detection values are read by all PDs, and the data of several points detected every 1 ms are averaged (step S3). Then, the averaged values are stored in the recording section (step S4). Similarly, in the next group, the emission for 10 ms, the measurement, and the data storage are repeated (steps S5, S6, and S2 through S4). Here, the emission of the four channels of the surface emitting laser array chip having an oscillation wavelength of 780 nm and the emission of the four channels of the surface emitting laser array chip having an oscillation wavelength of 900 nm are sequentially and similarly performed.

However, in the following data process, the two wavelengths are substantially similarly operated on, so that the measurement at the same position is performed two times in the same manner. Originally, in order to detect the change of blood flow, by using a difference obtained by using those two wavelengths, it becomes possible to separately detect oxygenated hemoglobin and reduced hemoglobin. However, in this embodiment, by using two surface emitting laser array chips having different oscillation wavelengths for measuring respective data, it becomes possible to reduce the noise caused by the differences between the chips.

After the emissions and the measurement of all the groups of the light source module LM are completed, the emission of the next light source module LM is performed (step S7, S8, and steps S2 through S4). Similar to the above, the emissions are sequentially performed on a group (4 channels) basis. After the emissions and the measurements of all the light source modules LM are completed, the light absorption body is set (steps S9 and S10). The light absorption body is set by using an optical stage so that the setting of the light absorption body can be accurately performed in a reproducible manner. In the state where the light absorption body is set, the emissions of the channels through the PD values recording are repeated (steps S2 through S9).

In the stored data, the data when there is the light absorption body and the data when there is no light absorption body are given as: "$r(s,i,n)(i=1, 2, 3, \ldots, M, n=1, 2, 3, \ldots, K)$" and "$r(0,i,n)(i=1, 2, 3, \ldots, M, n=1, 2, 3, \ldots, K)$", respectively. Here, the "i" denotes numbers that are allocated to the respective detection modules DM. The "n" denotes numbers that are allocated to respective groups. Next, respective differences $\Delta r(i,n)$ are calculated.

Figure 8:
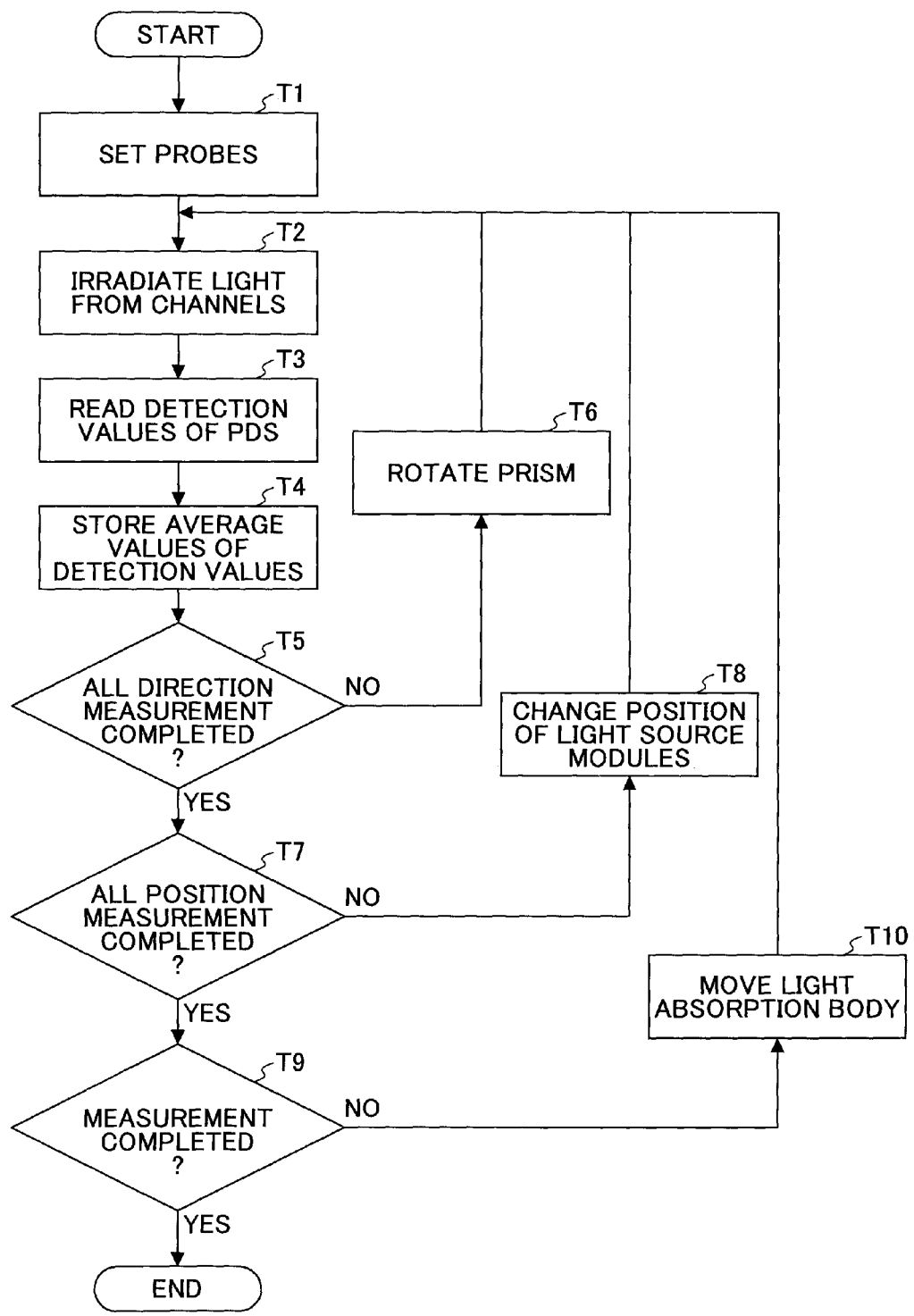
FIG. 8 is a flowchart illustrating a method of measuring information in an object under test.
Figure 9:
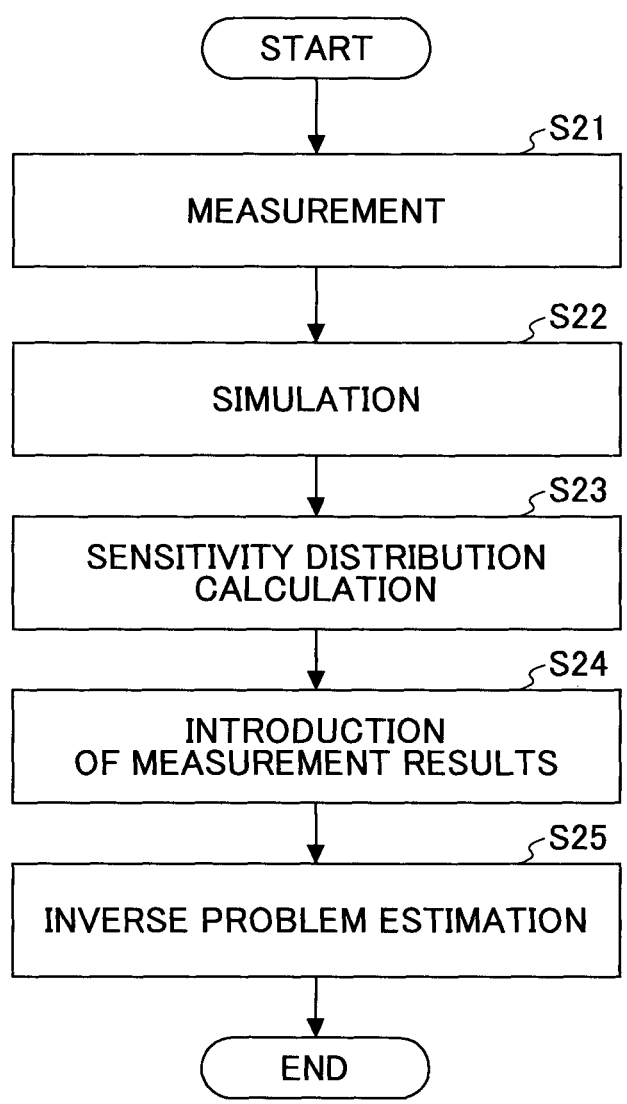
FIG. 9 is a flowchart related to an inverse problem estimation algorithm.

The method of calculating the position of the light absorption body (optical characteristic of the pseudo living body) based on the measurement results acquired by the position measurement method is similar to the method of calculating the position of the light absorption body (optical characteristic of the pseudo living body) based on the measurement results acquired by the measurement method based on the flowchart of FIG. 8. Therefore, the repeated description thereof is herein omitted.

As a result, it becomes possible to acquire the estimation result as illustrated in FIG. 31. FIG. 31 further illustrates a result of a comparative example where only one group at the center of the surface emitting laser array chip (see FIG. 17) emits and the detection is performed using the detection values of only one PD among the four PDs in the PD array. Other than this limitation, the numerical processing similar to that in the first embodiment is similarly performed. The configuration of this comparative example is similar to that in the NIRS (DOT) in related-art technology.

In this embodiment, based on a Bayesian estimation, it becomes possible to detect the position and the depth of the light absorption body. In the result illustrated in FIG. 31, a mark "○" (circle) is marked when the position of the light absorption body can be detected. In this embodiment, when the distance in the depth direction becomes greater, the distance from the light source module LM is increased and an amount of light that can be propagated is reduced. Due to this, the deeper the position of the light absorption body becomes, the more difficult the detection becomes. In this embodiment, it is possible to detect up to 16 mm. In the comparative example, due to a general NIRS (DOT) device, it is not possible to detection in the depth direction even when the Bayesian estimation is used. Generally, in order to highly-accurately detect a three-dimensional position of the light absorption body including the depth direction, it is necessary for the probes to be disposed in high density. However, in this embodiment, such highly-accurately detection can be performed with probes in low density.

The optical sensor 10 according to this embodiment (examples 1 and 2) as described above includes the irradiation system having the plural light source modules LM to irradiate light to the object under test (pseudo living body) and the detection system to detect the light irradiated from the irradiation system and propagated in the object under test. Further, each of the plural light source modules LM irradiate non-parallel plural light beams to the same position on the object under test.

In this case, the incident angles of the plural light beams, which are non-parallel to each other and irradiate onto the same position of the object under test (scattering body), in the object under test are different from each other, so that the plural light beams propagate in different propagation paths (see FIG. 32).

As a result, an amount of the acquired information related to the inside of the object under test is increased, so that higher resolution can be achieved. Further, due to the improved resolution, it becomes possible to achieve the same resolution by reducing the probe density (i.e., the number of probes per unit area), which makes it possible to improve the mountability (operability, installability).

As a result, it becomes possible for the optical sensor 10 to achieve a higher resolution without lowering the mountability onto the object under test.

Further, when the plural light beams that are incident on the same position of the object under test are non-parallel to each other, it means that the plural light beams form angles relative to each other. Namely, due to the existence of those angles of plural light beams formed relative to each other, it becomes possible to form different propagation paths by the plural light beams. On the other hand, if it is assumed that the plural light beams incident on the same position of the object under test are parallel to each other (e.g., if the plural light beams are parallel to the line normal to the surface of the object under test), the propagation paths of the plural lights in the object under test are the same as each other.

Further, the light source module LM according to this embodiment includes the surface emitting laser array having plural surface emitting lasers (light emitting sections) and the convex lens disposed on the optical paths of the plural light beams from the plural surface emitting lasers, so that the distance between the main point of the convex lens and the surface emitting laser array does not correspond to the focal length of the convex lens.

In this case, it becomes possible to prevent the concentration of the returned light beams on the surface emitting lasers so that it becomes possible to prevent the output change of the surface emitting lasers. As a result, it becomes possible to stabilize the amount of light emitted from the surface emitting lasers, improve the detection accuracy the optical sensor 10, and accordingly improve the resolution of the NIRS.

On the other hand, when the surface emitting laser array is disposed on the position of the focal point of the convex lens, the light beams reflected by the external reflection surface are concentrated on the surface emitting lasers by the convex lens, so that the laser oscillation becomes unstable. This phenomenon is called a "returned light" or a "self-mixing phenomenon". In a case where the surface emitting laser array is used as a light source of the optical sensor, if this phenomenon occurs, the amount of the emitted light becomes unstable (for more detail, see Japanese Laid-open Patent Publication Nos. 2011-114228 and 2012-132740).

Further, a transparent resin having a refractive index substantially equal to that of the convex lens fills in between the convex lens and the surface emitting laser array.

In this case, the refractive index does not change at the boundary surface between the convex lens and the surface emitting laser array. Therefore, the returned light can be reduced. As a result, it becomes possible to stabilize the amount of light emitted from the surface emitting laser array, and accordingly improve the resolution of the NIRS.

Further, the detection system includes plural detection modules DM, each having the plural light receive sections (PDs) that respectively receive the plural light beams irradiated from the light source module LM onto the object under test and propagated in the object under test.

In this case, it becomes possible to separately acquire two sets of information corresponding to two different propagation paths in the object under test.

Further, the detection module DM is disposed between the object under test and the plural light receive sections (PDs), and includes the contact member and the chassis having the respective apertures to pass a part of each of the plural light beams propagated in the object under test.

In this case, it become possible to take the light into the chassis through the same position of the object under test. Namely, it becomes possible to incident only the light whose incident angle is limited to some extent into the chassis from the object under test. By doing this, it becomes easier for the light to be incident onto the plural light receive sections.

Further, the detection module DM includes the division lens (light receive lens) that separately guides the part of the plural light beams, which has passed through the aperture, onto the plural light receive sections.

In this case, it becomes possible to separately incident a stable amount of a part of the respective plural light beams having passed through the aperture onto the plural light receive sections.

The light source module LM includes the window member to be in contact with the object under test and made of a material (transparent resin) having a refractive index greater than that of the object under test. Therefore, it becomes possible to set the propagation angle (refraction angle) in the object under test to be greater relative to the incident angle on the object under test. As a result, when compared with a case where the light is incident from air onto the object under test, the propagation angle becomes greater even when the incident angle is the same. Due to this, when compared with the difference in the incident angle between two light beams incident on the same position of the object under test at different incident angles, the difference in the propagation angle between the two light beams in the object under test becomes greater so that the propagation paths differs more greatly. As a result, it becomes possible to acquire higher resolution.

Further, the light source module LM includes plural surface emitting lasers arranged in a two dimensional manner and an irradiation lens (lens) disposed on a light path of the light from the plural surface emitting lasers.

In this case, it become possible to change the light propagation directions from the plural surface emitting lasers into desired directions (directions of the disposed corresponding prisms).

Further, the light source module LM is disposed on the light path of the light via the irradiation lens and includes the prism (reflection member) to reflect the light in a desired direction.

In this case, it is possible to further change the propagation direction of the light from the irradiation lens into a desired direction. Namely, it is possible to set the incident angle on the object under test to a desired angle.

As described above, by using the optical sensor 10, it becomes possible to achieve higher resolution by effectively using the light propagation anisotropy with a simple configuration, so as to be used in various fields such as the DOT, etc.

Further, the optical testing device 100 includes the optical sensor 10 and the control section (optical characteristic calculation section) to calculate the optical characteristics of the object under test based on the detection results acquired by the optical sensor 10.

In this case, due to the higher accuracy of the optical sensor 10, it becomes possible to highly-accurately calculate the optical characteristics of the object under test.

Second Embodiment

Next, a second embodiment of the present invention is described. In this embodiment, a method of adapting the probes, which are described in the first embodiment, to an actual human body is described. In this regard, it is assumed that the object under test is changed from the phantom (the water tank filled with white water) into a head part of a human body and the light absorption body is brain blood flow.

In this embodiment, an object is to accurately estimate the distribution of blood flow in brain. In this embodiment, a person under test (body under test) is measured, so that the figure is modeled based on the measured data and the Monte Carlo simulation is performed. The head shape of the person under test is measured by using a magnetic resonance imaging (MRI) method. Based on the images, the shapes of the four parts, namely the scalp, the skull bone, the cerebral fluid, and the brain cortex, are calculated.

The three-dimensional data may become necessary for highly-accurate detections. However, standard shape data of a brain model may alternatively be used. Those parts have the respective values of a scattering coefficient, anisotropy, and an absorption coefficient which are generally known. Therefore, those values are used. The probes are accurately fixed to the head with a fixing tool, and the setting position is accurately measured as well. The probes, etc., are the same as those in the first embodiment, and the repeated descriptions thereof are herein omitted. Here, optical simulation is performed based on the accurate shapes, positions, and values of the parts.

Figure 33:
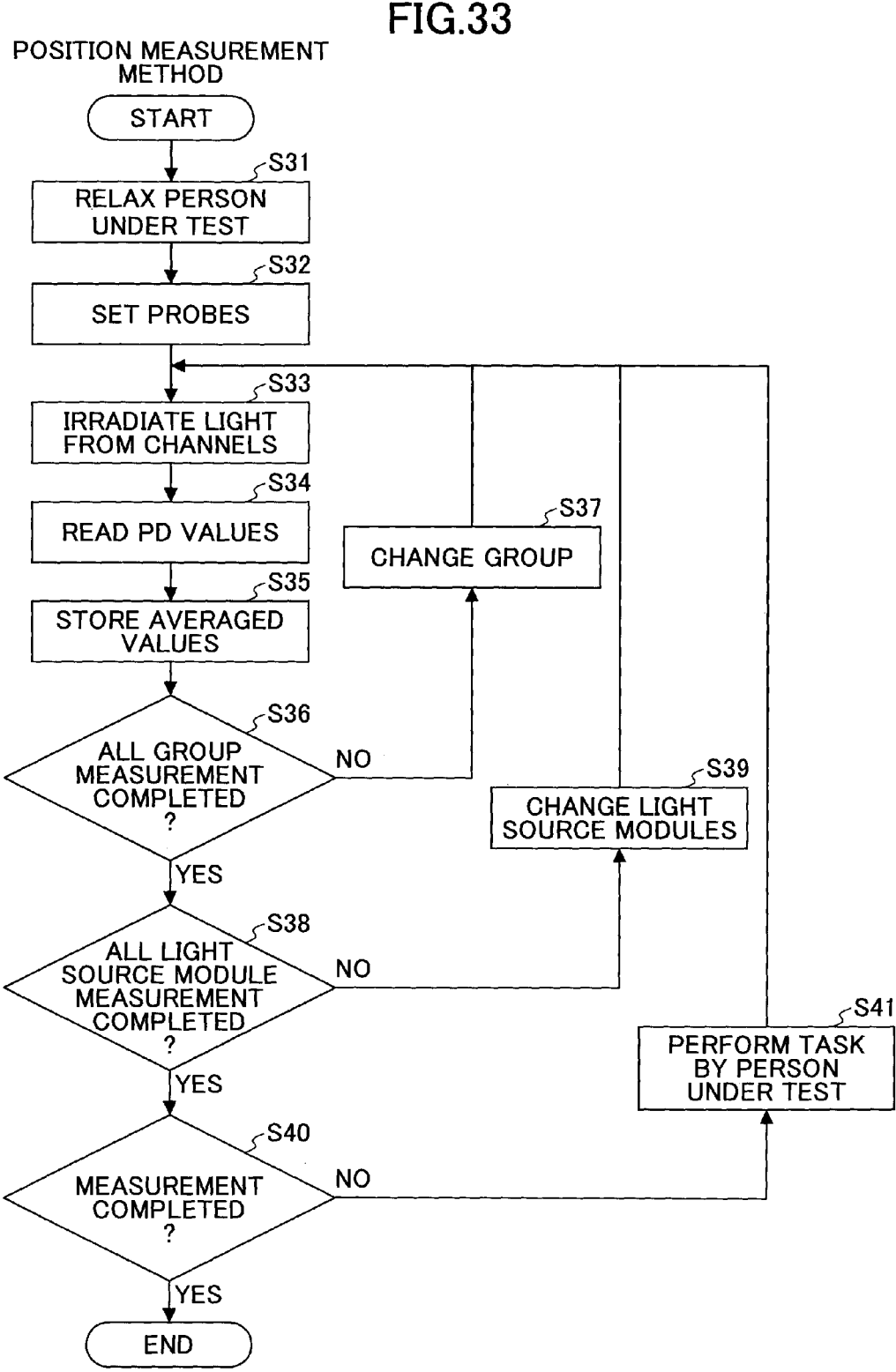
FIG. 33 is a flowchart of the optical characteristic detection method (position measurement method) according to the second embodiment.

In the following, a method of measuring the blood flow in a brain is described with reference to a flowchart of FIG. 33. First, the person under test is relaxed (step S31), and the probes (detection modules DM and light source modules LM) are attached to the head (step S32). In this case, the probes are carefully set (installed) one by one on the respective predetermined positions using a fixing member in a manner such that no hair and the like is sandwiched between the probes and the scalp. Under the set condition, channels are emitted (step S33). The emission (pulse emission) is performed on a group basis, and the current value is set so that the intensity is approximately 4 mW. The emission interval is about several ms. During the interval, the detection values of all the PDs are read and averaged (step S34). The average values are stored in a recording medium (step S35).

In the next group, the emission in the several ms, the measurement, and the data storage are similarly repeated (steps S36, S37, and S33 through S35). When the emissions and the measurements of all the light source modules LM are completed, the person under test is requested to perform a task (steps S38 through 41). Here, a general verbal fluency task is performed. Details of the verbal fluency task are described in Japanese Laid-open Patent Publication No. 2012-080975.

By performing the task, the brain is activated, so that brain blood flow occurs only at the activated parts. The blood flow includes oxygenated hemoglobin and reduced hemoglobin and light absorption occurs due to the blood flow. The inverse problem estimation, etc., by the Bayesian estimation accords to the method described in the above first embodiment, and accordingly, the repeated description is herein omitted. The accuracy of the blood flow positions acquired in this measurement can be checked by functional magnetic resonance imaging (fMRI). The "fMRI" refers to a method of visualizing a hemodynamic response related to the activity of the brain and the spinal cord of a human or an animal using the MRI. Based on the checking and the measurement, it is understood that the measurement with the optical sensor in this embodiment has a higher resolution.

Third Embodiment

Next, a third embodiment of the present invention is described. In the third embodiment, the light source modules LM and the detection modules DM similar to those in the first embodiment but the layout thereof is ingenious. Here, the descriptions other than the layout are the same as those in the first embodiment and the descriptions thereof are herein omitted.

In example 2 of the first embodiment, the light source modules LM and the detection modules DM are arranged in a manner such that two light source modules LM and two detection modules DM are arranged at the respective corners of a substantial square. However, if this layout is used, the length of the light path between the light source module LM and the detection module DM corresponding to the point indicated by the "x" mark in FIG. 15 is elongated. Due to this, it becomes difficult to obtain sufficient light amount by the detection module DM, so that the noise at this point may become greater and the detection accuracy may be lowered.

Figure 34:
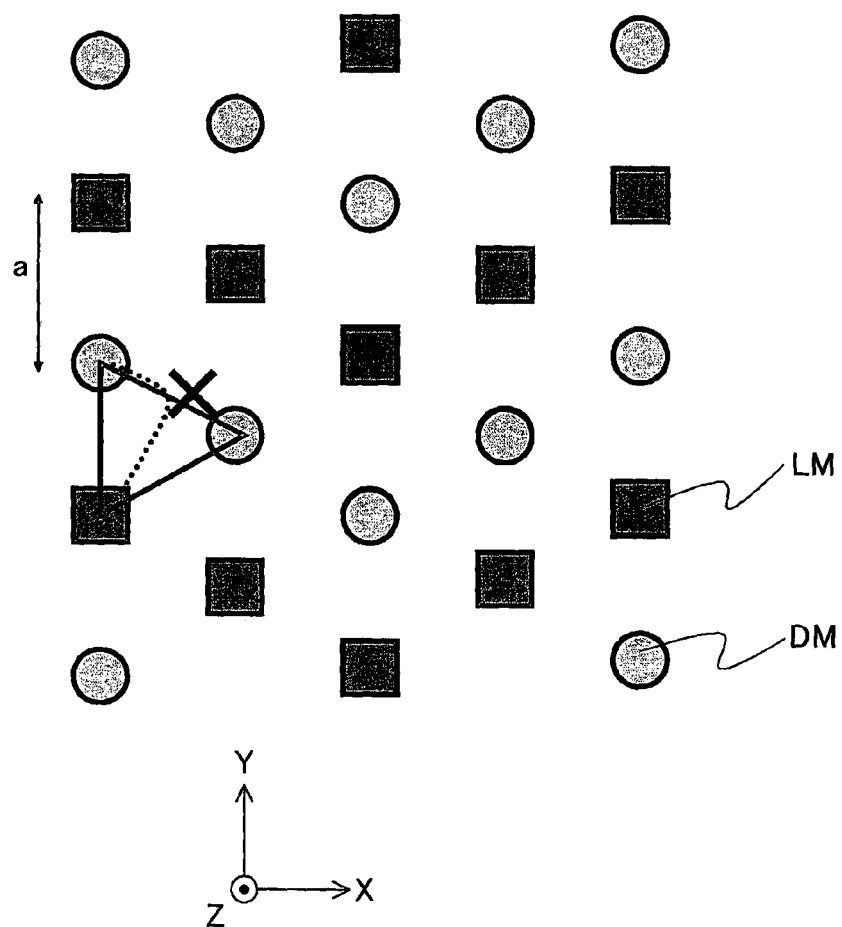
FIG. 34 is a drawing illustrating a layout of plural light source modules and plural detection modules in an optical sensor according to a third embodiment.

To resolve the problem, the inventors of the present invention have actively researched to determine an appropriate probe layout and have found that the layout illustrated in FIG. 34 is most suitable. In the layout in FIG. 34, the light source modules LM and the detection modules DM are arranged in a manner such that one of the light source module LM and the detection module DM is separately disposed at two corners of a regular triangle relative to the object under test and the other of the light source module LM and the detection module DM is arranged at the other corner of the regular triangle.

Here, as a simple example, the positions whose distances to the light source module LD and the detection module DM are the longest are compared. Here, it is assumed that the distance (pitch) between the light source module LD and the detection module DM is "a" in both cases. In the case of the position "x" in FIG. 15, the distance of the dotted line is calculated as $\sqrt{2}a$ (about 1.414a). On the other hand, in the case of the position "x" in FIG. 34, the distance of the dotted line is calculated as $(1+\sqrt{3})a/2$ (about 1.366a), which is less than $\sqrt{2}a$. Namely, when the longest distances are compared between the layouts in FIG. 15 and FIG. 34, the longest distance in FIG. 34 is shorter so that it is understood that the layout in FIG. 34 is preferable.

By using the probe layout according to this embodiment, it is understood that the detection area becomes wider as a result of inverse problem estimation which is performed in the same manner as that in the first embodiment.

Fourth Embodiment

Next, a fourth embodiment of the present invention is described. In the fourth embodiment, while the layout of the plural light source modules LM and the plural detection modules DM illustrated in the first embodiment is used, the layout of the channels of the light source module LM and the PDs of the detection module DM is ingenious. The descriptions other than the layout of the channels and the PDs are the same as those in the first embodiment. Therefore, the repeated descriptions thereof are herein omitted.

In example 2 of the first embodiment, as illustrated in FIG. 15, the plural light source modules LM and the plural detection modules DM are arranged in a manner such that the light source modules LM and the detection modules DM are adjacent to each other in both X and Y directions relative to the object under test.

However, as described above, the light path between the light source module LM and the detection module DM related to the position indicated by the "x" mark is elongated. Due to this, it becomes difficult to obtain a sufficient light amount by the detection module DM, so that noise at this point may become greater and the detection accuracy may be lowered.

Figure 35:
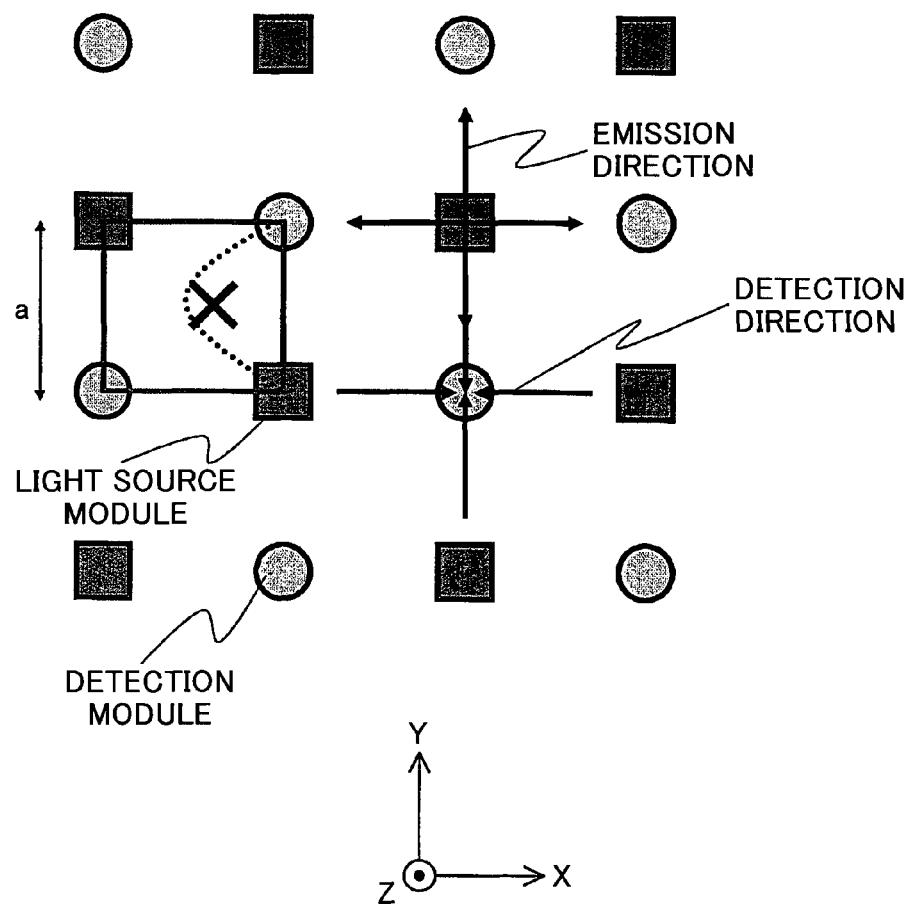
FIG. 35 is a drawing illustrating irradiation directions of the light source modules and detecting directions of the detection sensors in an optical sensor according to a comparative example.

In a comparative example of FIG. 35, the plural light source modules LM and the plural detection modules DM are arranged in a manner such that the light source modules LM and the detection modules DM are adjacent to each other in both X and Y directions relative to the object under test. Further, the emission directions and the detection detections (incident directions of the light on the light receive sections) are parallel to the X or Y direction. The lenses installed near the surface emitting lasers have point-symmetric optical characteristics. Due to this, the emission directions are determined based on the positions of the surface emitting lasers and the positions of the groups. Similarly, due to the point-symmetric optical characteristics of the lenses, the detection directions are determined based on the divided layout of the PD arrays.

Figure 36B:
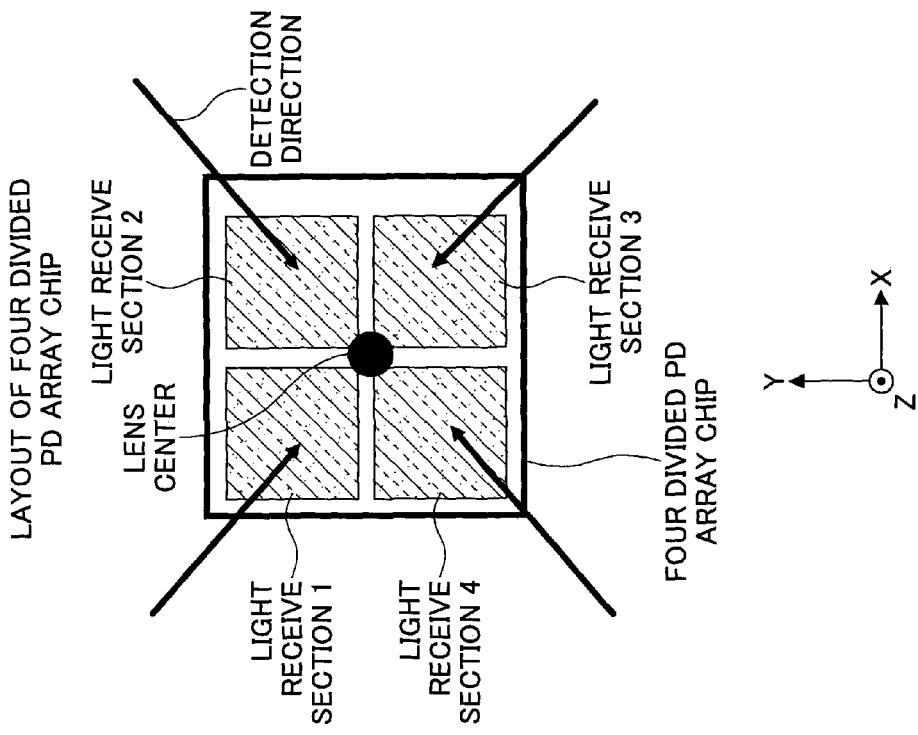
FIG. 36B is a drawing illustrating four PD detection directions of a PD array according to the fourth embodiment.
Figure 36A:
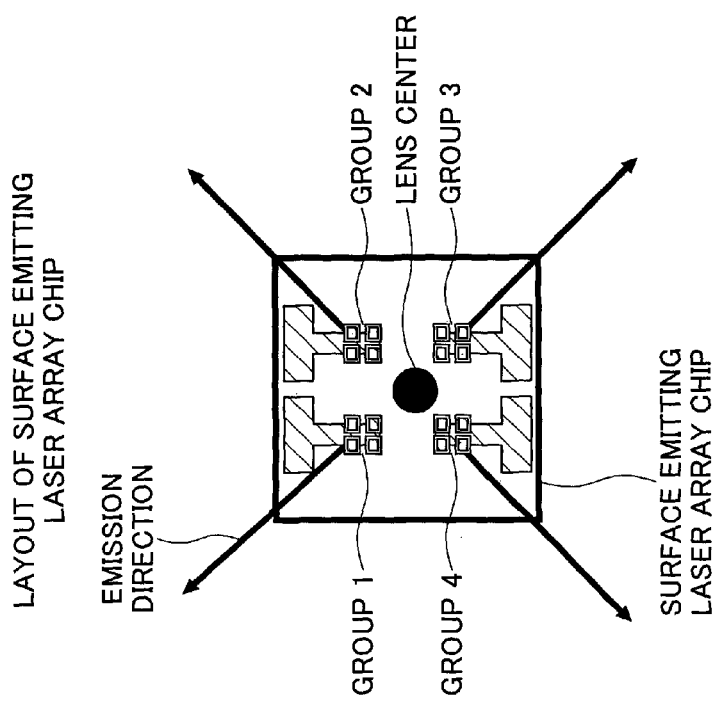
FIG. 36A is a drawing illustrating irradiation directions of four groups of surface emitting laser array chips according to a fourth embodiment.

In this regard, when the surface emitting laser array chip is disposed as illustrated in FIG. 36A, the emission directions are inclined relative to both the X direction and the Y direction in a planer view (when viewed from the +Z direction). This is because the center positions of the groups are inclined relative to the lens center. Similarly, in the detection module DM, by arranging the center of the lens at the chip center of the four divided PD array chip (photo diode array chip), the detection directions (the incident directions of light onto the light receive sections) are directions as illustrated in FIG. 36B. FIG. 37 illustrates the layout of the probes and the detection and emission directions. As illustrated in FIG. 37, it is understood that the emission directions and the detection directions are included relative to the X direction and the Y direction in a planer view (when viewed from the +Z direction).

In this case, similar to the sensitivity distribution described above, due to anisotropy of light, it is expected that more sensitivity may be obtained at the "x" marked position in FIG. 37.

As a result of the inverse problem estimation performed similar to the first embodiment using the layouts of FIGS. 36A and 36B, it is understood that the detectable area becomes larger (wider).

In the above embodiments, note than the number of the light source modules LM in the irradiation system and the number of the detection modules DM in the detection system may be appropriately changed. In short, the irradiation system may include at least one light source module LM and the detection system may include at least one detection module DM.

Further, note that the configuration of the light source module LM (light irradiator) may be appropriately changed. For example, the number and the layout of the surface emitting laser array chips of the light irradiator may be changed. Further, the type, the shape, the size, the number, etc., of the lenses may be appropriately changed.

Further, in the above embodiments, as the light sources of the light irradiator, the surface emitting lasers are used. However, for example, edge emitting lasers (LDs), light-emitting diodes (LEDs), organic EL elements, or lasers other than semiconductor lasers may alternatively be used.

In the above embodiments, prisms are used as the reflection members of the light irradiator. However, for example, another mirror or the like may alternatively be used.

Further, in the surface emitting laser array chip in example 2, the number and the layout of the groups and the number and the layout of the channels of the groups may alternatively be changed.

Further, the configuration of the detection module (DM) (light detector) may alternatively be changed. For example, the aperture may not be formed. Further, the division lens may not be used.

Further, it is needless to say that the figure (shape), the size, the number, the dimensions, the value of the members and parts may be alternatively be changed.

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

The present application is based on and claims the benefit of priority of Japanese Patent Application Nos. 2013-203155 filed Sep. 30, 2013 and 2014-163363 filed on Aug. 11, 2014, the entire contents of which are hereby incorporated herein by reference.

DESCRIPTION OF THE REFERENCE NUMERALS

10: OPTICAL SENSOR
100: OPTICAL TESTING DEVICE
LM: LIGHT SOURCE MODULE
DM: DETECTION MODULE

PRIOR ART DOCUMENTS

Patent Document

[Patent Document 1] Japanese Patent No. 3779134

The invention claimed is:

1. An optical sensor comprising:
an irradiation system including at least one light irradiator to irradiate light beams onto an object under test; and
a detection system configured to detect the light beam that is irradiated from the irradiation system and is propagated in the object under test,
wherein the light irradiator includes plural light emitting sections that are independently controllable, and the light irradiator including the plural light emitting sections irradiates non-parallel plural respective light beams on a same position of the object under test,
wherein the light irradiator includes a surface emitting laser array and a lens, the lens being disposed on light paths of plural light beams from the plural light emitting sections and changing the plural light beams into the non-parallel plural light beams,
a size of an external form of the surface emitting laser array (dmax) is substantially equivalent to a size of the lens (ε), and
a difference (L−f) between (i) a distance L between a main point of the lens and the surface emitting laser array and (ii) a focal length f of the lens satisfies the following equation (1):

$$-1000\ \mu m < (L-f) < 1000\ \mu m \tag{1}$$

2. The optical sensor according to claim 1,
wherein the lens has a convex shape on the surface emitting laser array.

3. An optical testing device comprising:
the optical sensor according to claim 1;
an optical characteristic calculation unit configured to calculate an optical characteristic of the object under test based on a detection result by the optical sensor.

4. The optical sensor according to claim 1, wherein the distance L between the main point of the lens and the surface emitting laser array is substantially equivalent to the focal length f of the lens, and each of the distance L and the focal length f is greater than a height of a wire to feed electrical power to the surface emitting laser array.

5. An optical sensor comprising:
an irradiation system including at least one light irradiator to irradiate light onto an object under test; and
a detection system configured to detect the light that is irradiated from the irradiation system and is propagated in the object under test,
wherein the light irradiator irradiates non-parallel plural light beams on a same position of the object under test, wherein the light irradiator includes a surface emitting laser array and a lens, the surface emitting laser array having plural light emitting sections, the lens being disposed on light paths of the plural light beams from the plural light emitting sections and changing the plural light beams into the non-parallel plural light beams, and a distance between a main point of the lens and the surface emitting laser array is not equal to a focal length of the lens, and wherein a transparent resin having a refractive index equal to the refractive index of the lens fills in between the lens and the surface emitting laser array.

6. An optical testing device comprising:
the optical sensor according to claim 5;
an optical characteristic calculation unit configured to calculate an optical characteristic of the object under test based on a detection result by the optical sensor.

7. An optical characteristic detection method of detecting an optical characteristic of an object under test using the optical sensor according to claim 5, comprising:
a step of acquiring a sensitivity distribution of the object under test relative to light; and
a step of calculating the optical characteristic of the object under test by resolving an inverse problem based on the sensitivity distribution.

8. An optical sensor comprising:
an irradiation system including at least one light irradiator to irradiate light onto an object under test; and
a detection system configured to detect the light that is irradiated from the irradiation system and is propagated in the object under test,
wherein the light irradiator irradiates non-parallel plural light beams on a same position of the object under test,
wherein the light irradiator includes a surface emitting laser array and a lens, the surface emitting laser array having plural light emitting sections, the lens being disposed on light paths of the plural light beams from the plural light emitting sections and changing the plural light beams into the non-parallel plural light beams, and
a distance between a main point of the lens and the surface emitting laser array is not equal to a focal length of the lens, and
wherein the detection system includes at least one light detector having plural light receive sections that receive the plural light beams irradiated from the light irradiator and propagated in the object under test.

9. The optical sensor according to claim 8,
wherein the light detector includes a member that is disposed between the object under test and the plural light receive sections and has a passage section to pass a part of each of the plural light beams propagated in the object under test.

10. The optical sensor according to claim 9,
wherein the light detector includes a light receive lens that guides the part of the plural light beams having passed through the passage section onto the plural light receive sections.

11. The optical sensor according to claim 8,
wherein the irradiation system includes a plurality of light irradiators and the detection system includes a plurality of light detectors,
the light irradiators and the light detectors are arranged in a manner such that the light irradiators and the light detectors are adjacent to each other in both of two directions, which are orthogonal to each other, relative to the object under test,
emission directions of the plural light beams from the respective plural light irradiators are inclined relative to the two directions, and
incident directions of the plural light beams propagated in the object under test and incident on the light detectors are inclined relative to the two directions.

12. The optical sensor according to claim 8,
wherein the irradiation system includes a plurality of light irradiators and the detection system includes a plurality of light detectors, and
the light irradiators and the light detectors are arranged in a manner such that one of the light irradiator and the light detector is separately disposed at two corners of a regular triangle relative to the object under test and the other of the light irradiator and the light detector is disposed at the other corner of the regular triangle.

13. An optical testing device comprising:
the optical sensor according to claim 8;
an optical characteristic calculation unit configured to calculate an optical characteristic of the object under test based on a detection result by the optical sensor.

14. An optical characteristic detection method of detecting an optical characteristic of an object under test using the optical sensor according to claim 8, comprising:
a step of acquiring a sensitivity distribution of the object under test relative to light; and
a step of calculating the optical characteristic of the object under test by resolving an inverse problem based on the sensitivity distribution.

15. An optical sensor comprising:
an irradiation system including at least one light irradiator to irradiate light beams onto an object under test; and
a detection system configured to detect the light beam that is irradiated from the irradiation system and is propagated in the object under test,
wherein the light irradiator includes plural light emitting sections that are independently controllable, and the light irradiator including the plural light emitting sections irradiates non-parallel plural respective light beams on a same position of the object under test,
wherein the light irradiator includes a surface emitting laser array and a lens, the lens being disposed on light paths of plural light beams from the plural light emitting sections and changing the plural light beams into the non-parallel plural light beams,
wherein a distance between a main point of the lens and the surface emitting laser array is not equal to a focal length of the lens, and
wherein the light irradiator includes an optical element having a reflection surface that is disposed on a light path of the light via the lens and that is configured to reflect the light in a desired direction, towards and to another surface configured to be in contact with the object under test.

16. The optical sensor according to claim 15,
wherein the optical element of the light irradiator having the surface configured to be in contact with the object under test has a greater refractive index than air.

17. The optical sensor according to claim 15,
wherein the reflection surface of the light irradiator is a surface of a prism.

18. An optical characteristic detection method of detecting an optical characteristic of an object under test using an optical sensor comprising:

an irradiation system including at least one light irradiator to irradiate light beams onto an object under test; and
a detection system configured to detect the light beam that is irradiated from the irradiation system and is propagated in the object under test,
wherein the light irradiator includes plural light emitting sections that are independently controllable, and the light irradiator including the plural light emitting sections irradiates non-parallel plural respective light beams on a same position of the object under test,
the optical characteristic detection method comprising:
a step of acquiring plural sensitivity distributions of the object under test relative to the light beams; and
a step of calculating the optical characteristic of the object under test by using sensitivity distributions amongst the plural sensitivity distributions which differ from each other depending on the light beams having different directivities, and by resolving an inverse problem based on the sensitivity distribution.

* * * * *

UNITED STATES PATENT AND TRADEMARK OFFICE
CERTIFICATE OF CORRECTION

PATENT NO. : 10,039,452 B2
APPLICATION NO. : 14/913754
DATED : August 7, 2018
INVENTOR(S) : Toshihiro Ishii et al.

It is certified that error appears in the above-identified patent and that said Letters Patent is hereby corrected as shown below:

On the Title Page

Replace item (73), with the following:
--(73) Assignees: RICOH COMPANY, LTD., Tokyo (JP);
                  ADVANCED TELECOMMUNICATIONS RESEARCH INSTITUTE
                  INTERNATIONAL, Kyoto (JP).--

Signed and Sealed this
Twenty-fifth Day of February, 2020

Andrei Iancu
*Director of the United States Patent and Trademark Office*